United States Patent
Chen et al.

(10) Patent No.: US 11,250,601 B2
(45) Date of Patent: Feb. 15, 2022

(54) LEARNING-ASSISTED MULTI-MODALITY DIELECTRIC IMAGING

(71) Applicant: UNIVERSITY OF SOUTHERN CALIFORNIA, Los Angeles, CA (US)

(72) Inventors: Guanbo Chen, Allen, TX (US); Mahta Moghaddam, Los Angeles, CA (US); Pratik Shah, Vista, CA (US); John Stang, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 95 days.

(21) Appl. No.: 16/839,853

(22) Filed: Apr. 3, 2020

(65) Prior Publication Data
US 2020/0320752 A1 Oct. 8, 2020

Related U.S. Application Data

(60) Provisional application No. 62/843,441, filed on May 4, 2019, provisional application No. 62/828,738, filed on Apr. 3, 2019.

(51) Int. Cl.
*G06T 11/00* (2006.01)
*G06T 7/00* (2017.01)
(Continued)

(52) U.S. Cl.
CPC .......... *G06T 11/006* (2013.01); *A61B 5/055* (2013.01); *A61B 6/032* (2013.01); *A61B 8/00* (2013.01);
(Continued)

(58) Field of Classification Search
None
See application file for complete search history.

(56) References Cited

U.S. PATENT DOCUMENTS

| 6,377,872 B1* | 4/2002 | Struckman | E02F 9/205 |
| | | | 342/459 |
| 8,724,864 B2* | 5/2014 | Persson | A61B 5/6804 |
| | | | 382/128 |

(Continued)

OTHER PUBLICATIONS

S. Caorsi and P. Gamba, "Electromagnetic detection of dielectric cylinders by a neural network approach," IEEE transactions on geoscience and remote sensing, vol. 37, No. 2, pp. 820-827, 1999 (Year: 1999).*

(Continued)

*Primary Examiner* — Gandhi Thirugnanam
(74) *Attorney, Agent, or Firm* — Brooks Kushman P.C.

(57) ABSTRACT

A Convolutional Neural Network (CNN) assisted dielectric imaging method is provided. The method used CNN to incorporate the abundant image information from Magnetic Resonance (MR) images into the inverse scattering model-based microwave imaging process and generate high-fidelity dielectric images. A CNN is designed and trained to learn the complex mapping function from MR T1 images to dielectric images. Once trained, the new patients' MR T1 images are fed into the CNN to generate predicted dielectric images, which are used as the starting image for the microwave inverse scattering imaging. The CNN-predicted dielectric image significantly reduces the non-linearity and ill-posedness of the inverse scattering problem. The application of the proposed method to recover human brain dielectric images at 4 mm and 2 mm resolution with single-frequency and multi-frequency microwave measurements is provided.

21 Claims, 22 Drawing Sheets
(10 of 22 Drawing Sheet(s) Filed in Color)

(51) Int. Cl.
G06T 7/11 (2017.01)
G06N 3/08 (2006.01)
G16H 30/20 (2018.01)
A61B 5/055 (2006.01)
A61B 8/00 (2006.01)
A61B 6/03 (2006.01)

(52) U.S. Cl.
CPC ............ *G06N 3/08* (2013.01); *G06T 7/0012* (2013.01); *G06T 7/11* (2017.01); *G16H 30/20* (2018.01); *G06T 2207/10081* (2013.01); *G06T 2207/10088* (2013.01); *G06T 2207/10132* (2013.01); *G06T 2207/20081* (2013.01); *G06T 2207/20084* (2013.01); *G06T 2207/30004* (2013.01)

(56) References Cited

U.S. PATENT DOCUMENTS

| | | | | |
|---|---|---|---|---|
| 9,386,936 | B2* | 7/2016 | McCollough | G16H 30/40 |
| 2006/0241410 | A1* | 10/2006 | Fang | A61B 5/05 600/430 |
| 2017/0261538 | A1* | 9/2017 | Kamilov | G06N 3/084 |
| 2020/0320752 | A1* | 10/2020 | Chen | A61B 5/0035 |
| 2021/0196207 | A1* | 7/2021 | Shamir | G16H 50/20 |

OTHER PUBLICATIONS

U. S. Kamilov, D. Liu, H. Mansour, and P. T. Boufounos, "A recursive born approach to nonlinear inverse scattering," IEEE Signal Processing Letters, vol. 23, No. 8, pp. 1052-1056, 2016 (Year: 2016).*

Z. Wei and X. Chen, "Deep-learning schemes for full-wave nonlinear inverse scattering problems," IEEE Transactions on Geoscience and Remote Sensing, 2018 (Year: 2018).*

Chen, G. et al., "Multi-parameter microwave inverse scattering with group sparsity constraints," in Proc. IEEE Int. Symp. Antennas Propag. USNC/URSI Nat. Radio Sci. Meeting, Jul. 2018, pp. 697-698.

Chen, G. et al., "Learning-Assisted Multimodality Dielectric Imaging," in IEEE Transactions on Antennas and Propagation, vol. 68, No. 3, Mar. 2020, pp. 2356-2369.

Shah, P. et al., "Inverse scattering using a joint l1-l2 norm-based regularization," IEEE Transactions on Antennas and Propagation, vol. 64, No. 4, 2016, pp. 1373-1384 2016.

Shah, P. et al., "A fast level set method for multimaterial recovery in microwave imaging," IEEE Transactions on Antennas and Propagation, vol. 66, No. 6, 2018, pp. 3017-3026.

* cited by examiner

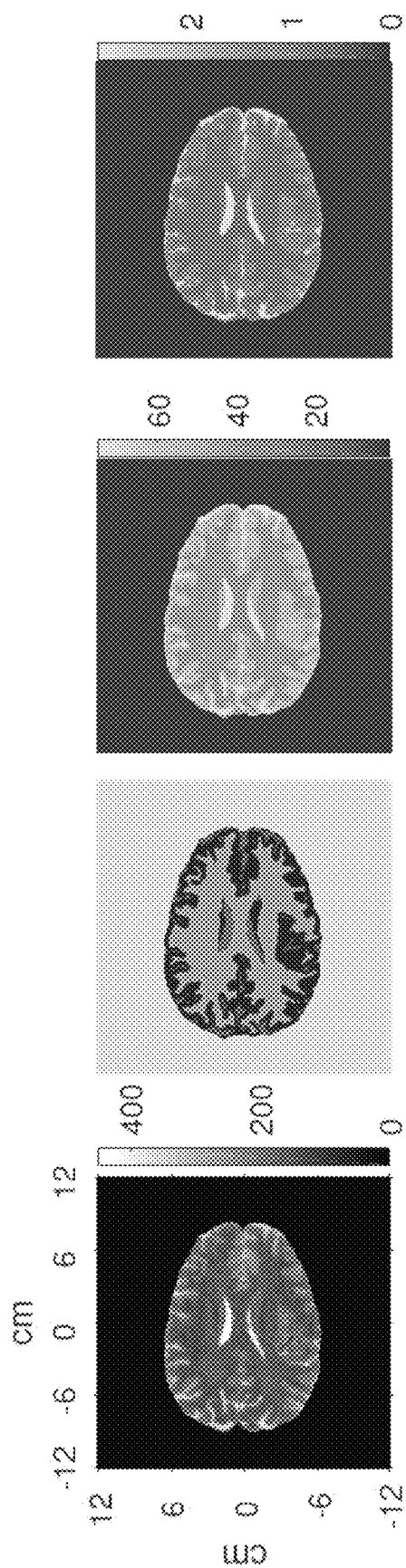
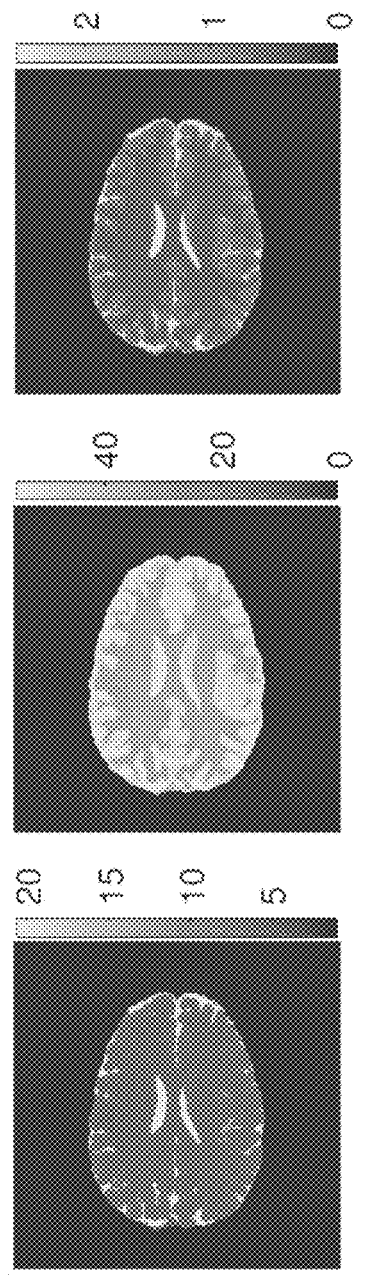
Fig. 3A  Fig. 3B  Fig. 3C  Fig. 3D
Fig. 3E  Fig. 3F  Fig. 3G

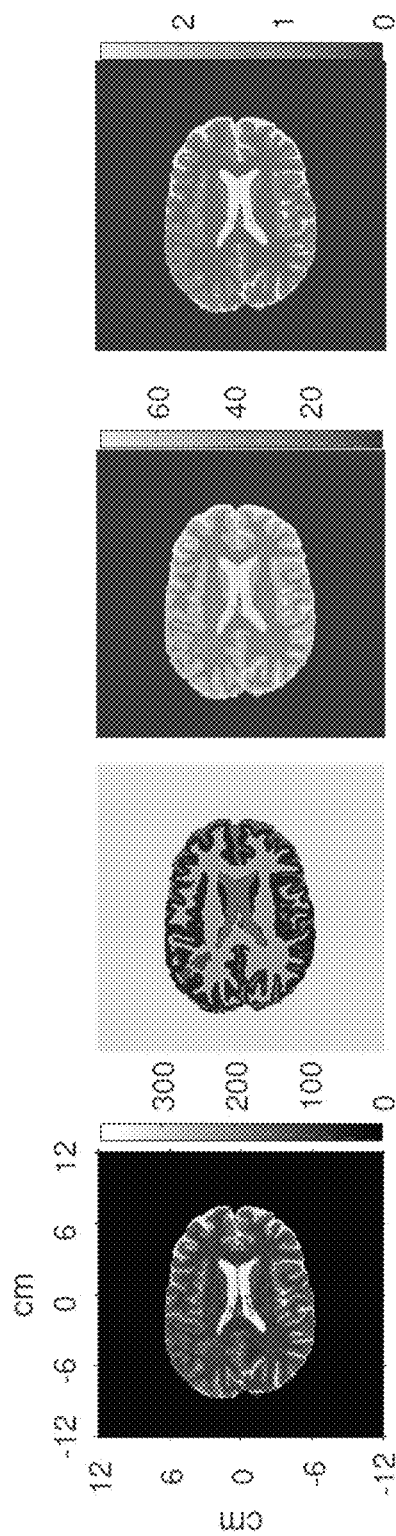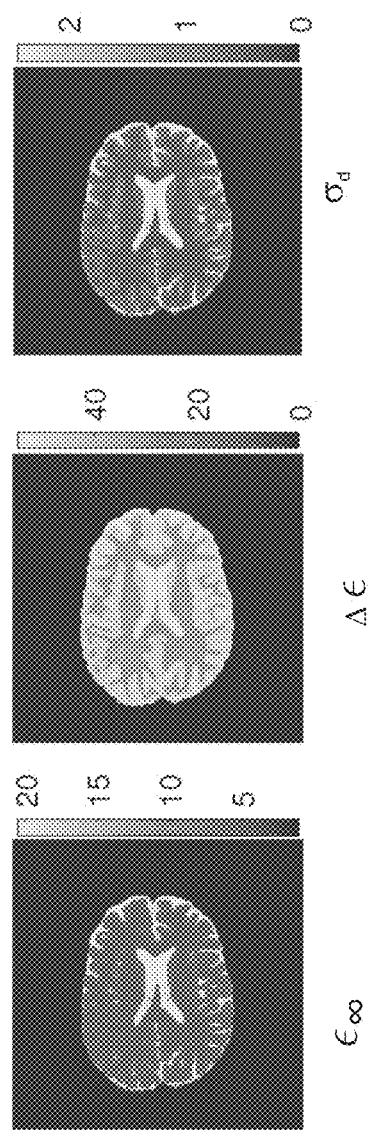

Map T2 to $\epsilon$

Map T2 to $\sigma$

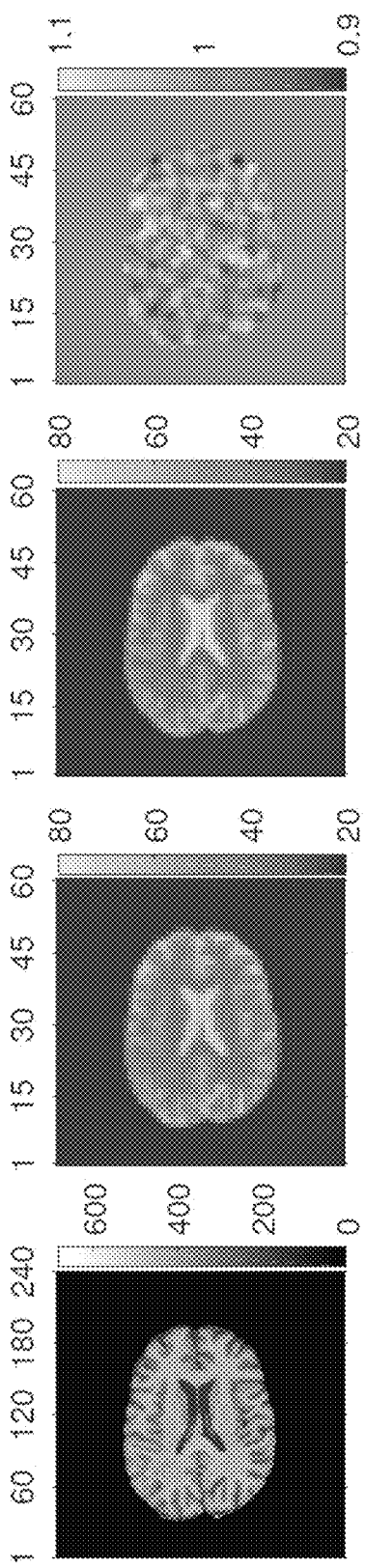
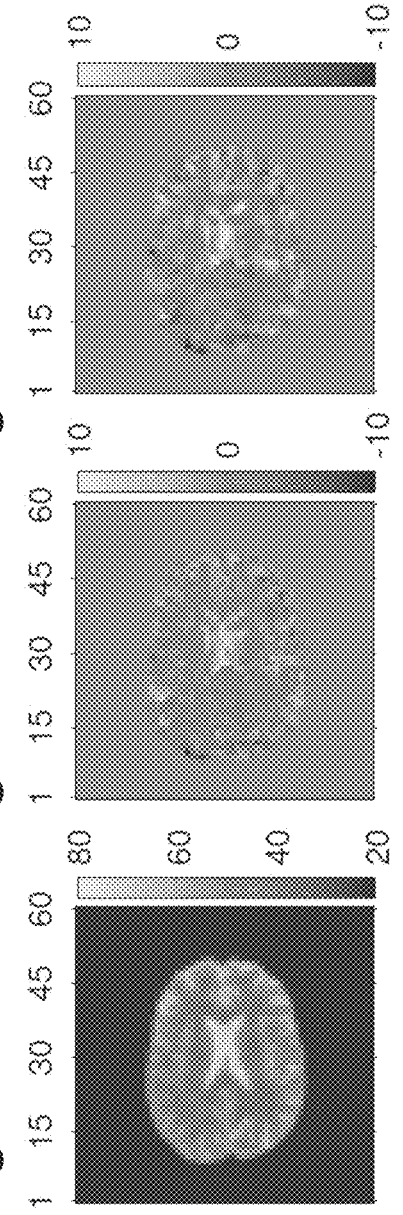
Fig. 12A  Fig. 12B  Fig. 12C  Fig. 12D
Fig. 12E  Fig. 12F  Fig. 12G

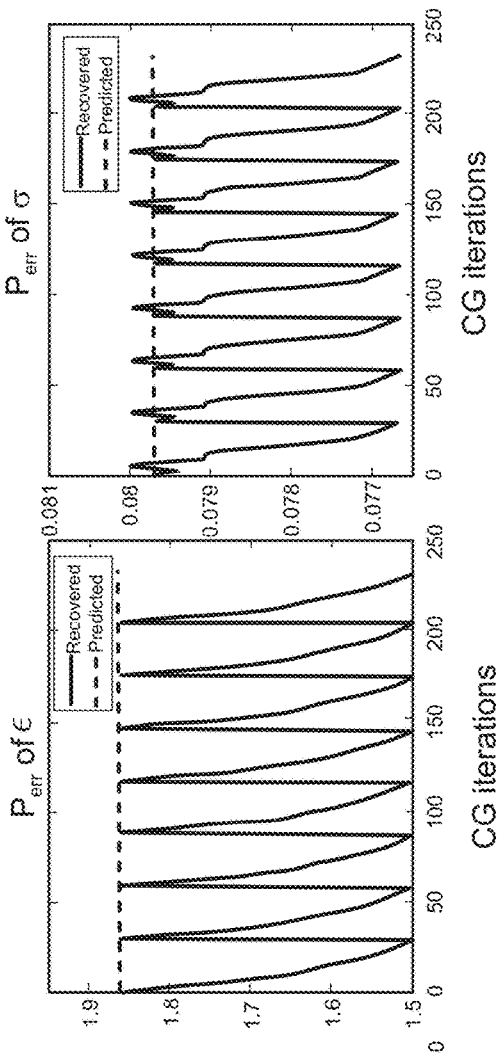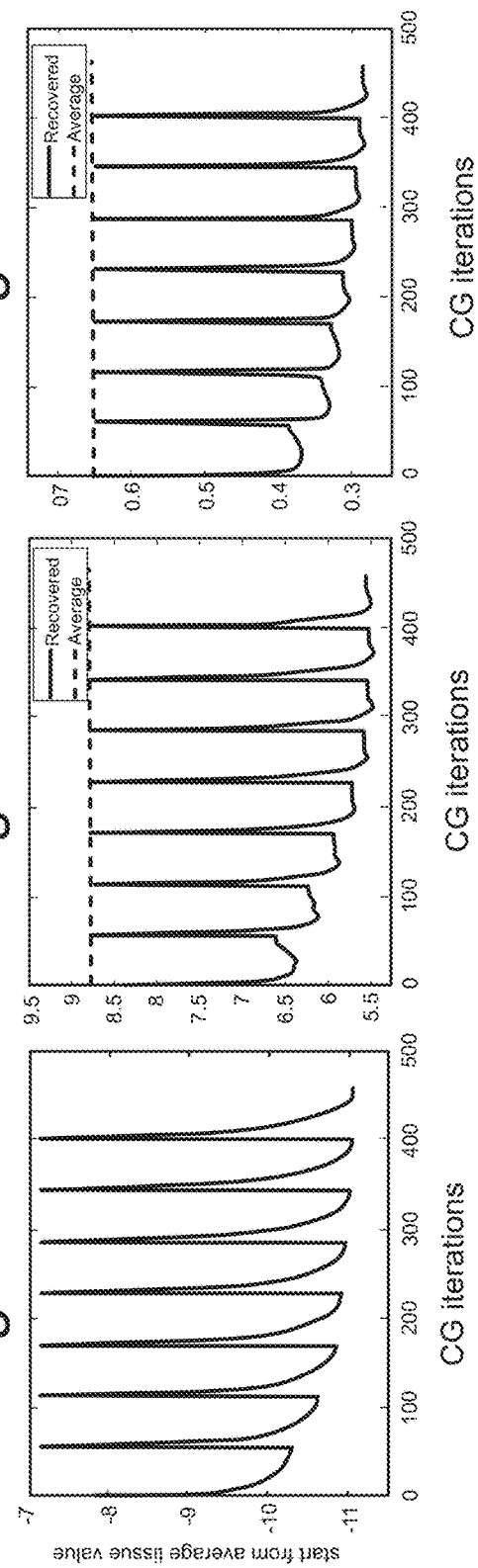
Fig. 15A  Fig. 15B  Fig. 15C
Fig. 15D  Fig. 15E  Fig. 15F

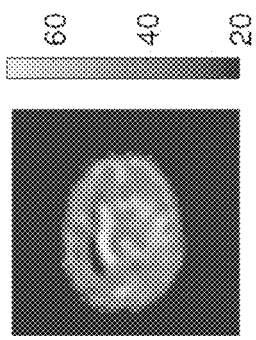 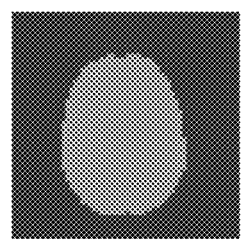 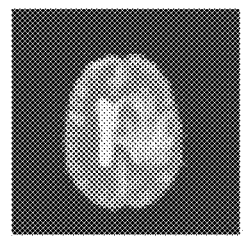 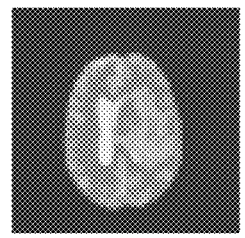 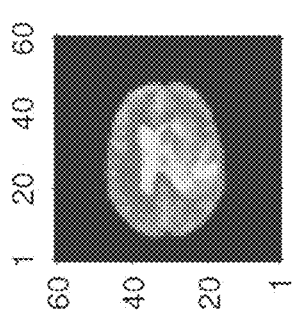
Fig. 16A  Fig. 16B  Fig. 16C  Fig. 16D  Fig. 16E
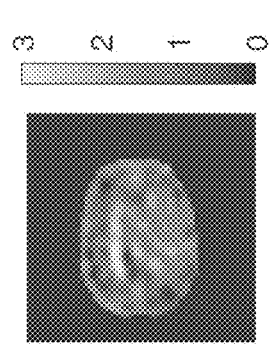 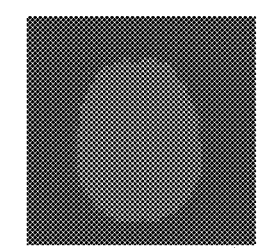 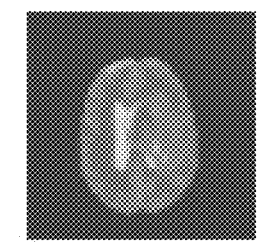
Fig. 16F  Fig. 16G  Fig. 16H  Fig. 16I  Fig. 16J

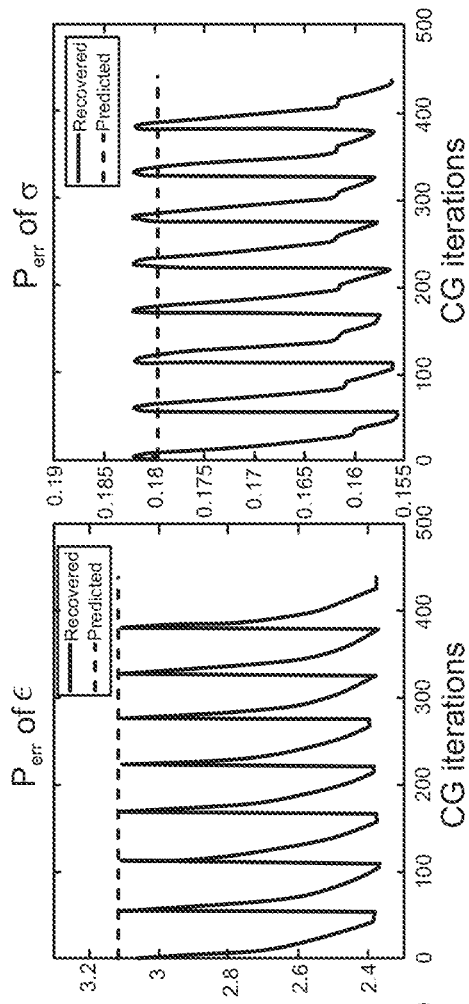
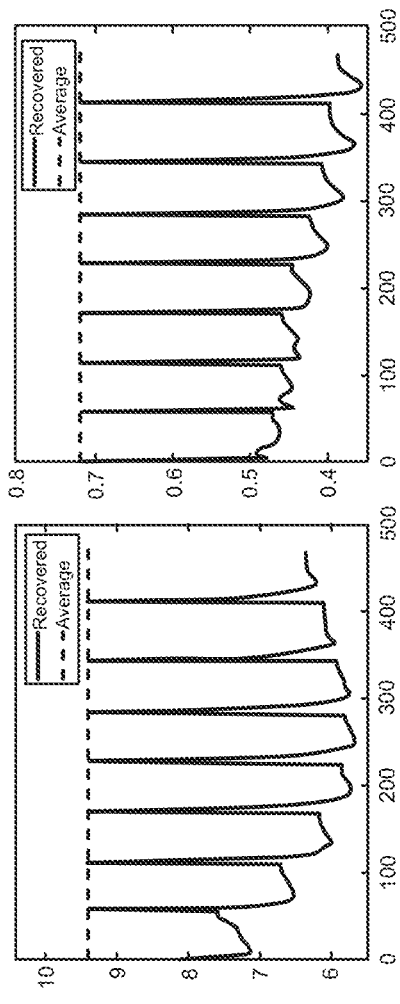
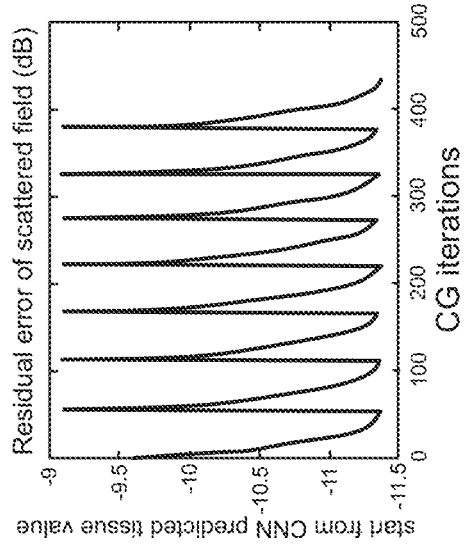
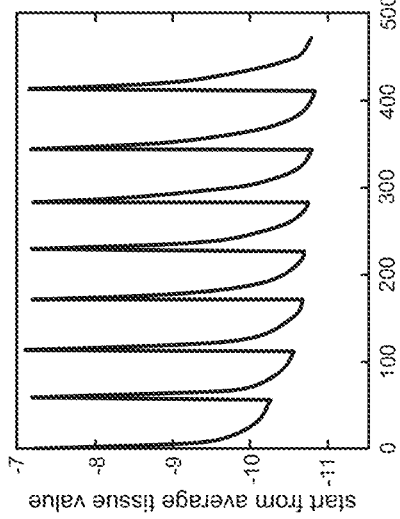
Fig. 17A  Fig. 17B  Fig. 17C
Fig. 17D  Fig. 17E  Fig. 17F

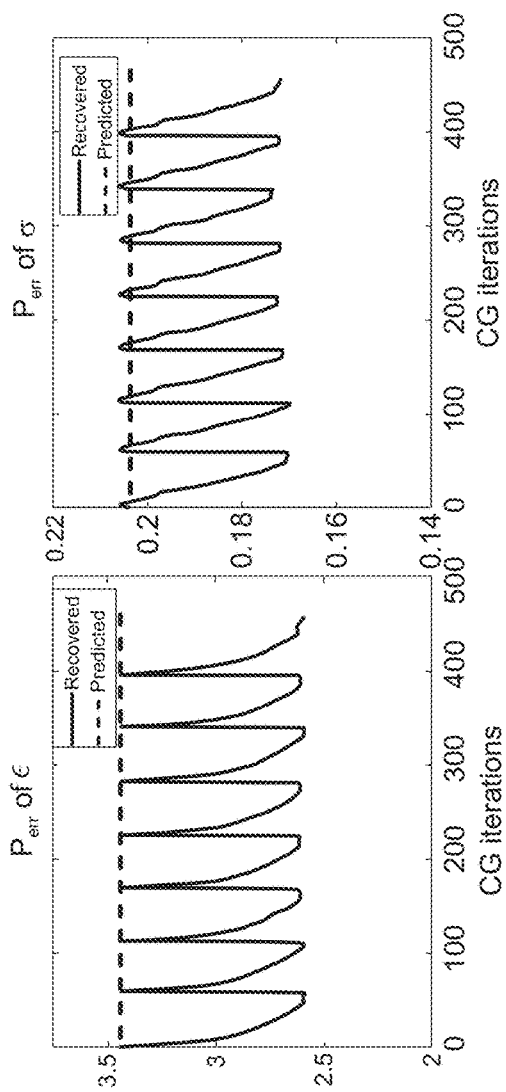
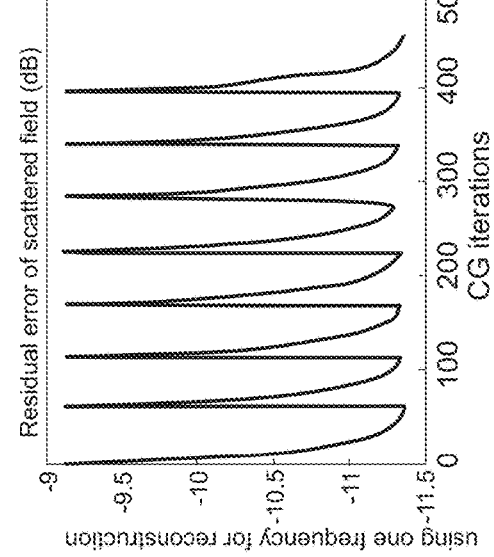
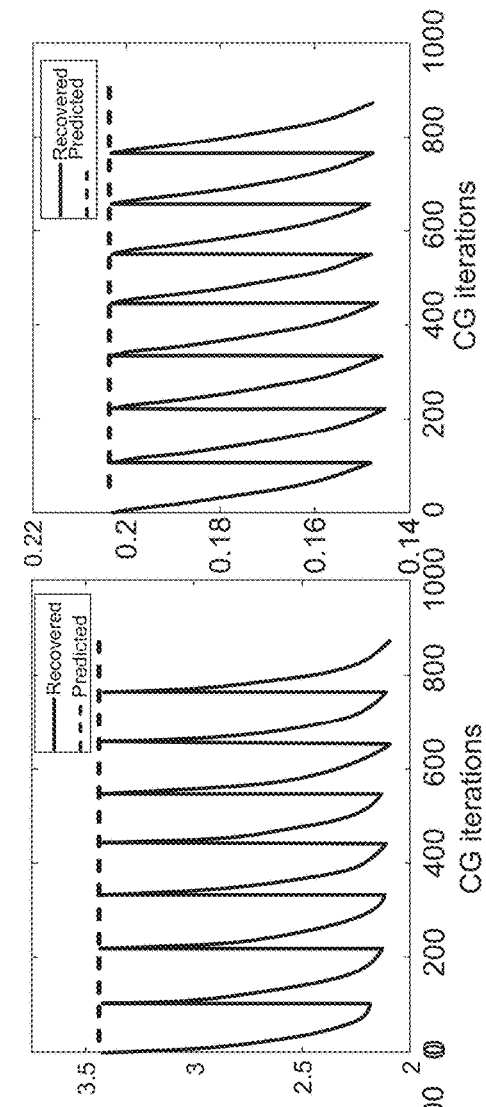
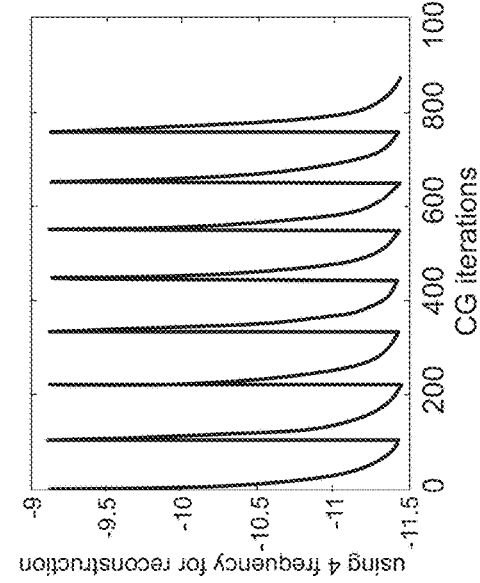
Fig. 20A  Fig. 20B  Fig. 20C
Fig. 20D  Fig. 20E  Fig. 20F

LEARNING-ASSISTED MULTI-MODALITY DIELECTRIC IMAGING

CROSS-REFERENCE TO RELATED APPLICATIONS

This application claims the benefit of U.S. provisional application Ser. No. 62/828,738 filed Apr. 3, 2019 and U.S. provisional application Ser. No. 62/843,441 filed May 4, 2019, the disclosures of which are hereby incorporated in their entirety by reference herein.

TECHNICAL FIELD

In at least one aspect, the present invention is related medical imaging techniques.

BACKGROUND

Dielectric images, which provide the permittivity and conductivity information of an object, have shown great potentials in a wide range of biomedical applications, such as medical diagnostics, thermal therapy monitoring and bioelectronics studies, etc. [1]. Dielectric images can be acquired noninvasively through microwave inverse scattering imaging. However, due to the ill-posedness, nonlinearity and non-uniqueness of microwave imaging problem [2], current microwave imaging methods have not yet generated dielectric images of sufficient quality for broad clinical use.

To address these challenges, physical-model-based optimization methods [3] [4] [5] and artificial neural-network-based learning methods [6] [7] have been proposed and investigated for microwave imaging. For the physical-model-based iterative optimization methods, the fields (or contrast sources) and the dielectrics are solved sequentially in each iteration to alleviate the nonlinearity of the problem. In addition, to address the non-uniqueness, regularization methods with different prior assumptions are used to choose a preferred solution. Among them, Tikhonov regularization [8] is used when the objects are assumed to be smooth with few high spatial frequency components. When the objects are assumed to be sparse or group sparse, $L\_1$[9, 10], $L\_1,2$ [11] norm constrained regularizations are used, which help to preserve the edge and sharpness of the object. When the number of distinct dielectric objects is assumed known, this prior knowledge can be introduced with the level-set based optimization method [12] [13]. For the learning based methods, artificial neural networks have been proposed to assist or replace the physical models during the inversion. Those methods have seen improved results at the cost of limited applicability [14-16] or the extra computational cost for training [6][7].

The information used in the microwave imaging methods mentioned above are only limited to the scattered fields measured with a microwave imaging system and the simple prior assumptions enforced with different regularization methods. To utilize more information, another approach is to incorporate the abundant information obtained from other imaging modalities to assist and improve the dielectric image reconstruction, such as [17-20]. Specifically, the Magnetic Resonance (MR) image derived spatial distribution of different types of tissues are incorporated as a spatial prior into the microwave imaging process [19, 20]. The spatial priors are incorporated as soft priors, where pixels/voxels of the same tissue-type have the same weight in the $L\_2$ norm regularized weighting matrix. This method has been tested on numerical 3D breast phantoms [21] and in experimental setups [22]. These methods have shown improved imaging results compared with traditional methods; however, the image tissue type segmentation has to be performed for each new case to get the spatial prior.

SUMMARY

In at least one aspect, a fundamentally different Convolutional Neural Network (CNN) based multi-modality dielectric imaging method is provided. This method can effectively and efficiently incorporate both the structure and the tissue property information acquired from other imaging modalities into the dielectric image reconstruction process. The method includes at least three steps: First, the complex mapping function from MR/Computed Tomography (CT)/Ultrasound images to dielectric images is learned by training a CNN. Then, for each new patient, the trained CNN can take in their MR/CT/Ultrasound images and produce predicted dielectric images. Lastly, the predicted dielectric images are used as the starting or prior images for physics-model-based iterative dielectric image reconstruction. As a result, the CNN-predicted dielectric images significantly alleviate the nonlinearity and ill-posedness of the physics-based inversion model, and the physics-based inversion model will complement the CNN by recovering information missing in the training data and not learned by the CNN. Compared with the previous multi-modality microwave imaging methods, our CNN-based approach has two main advantages: (1) for each new case (new patient), the CNN-based approach can avoid performing complicated tissue segmentation of other modalities' image for information extraction. The relationships between any modality's image data and the corresponding dielectric image is learned and stored in the CNN (2) Besides the information about the spatial distribution of each tissue, the CNN captures more detailed pixel-level tissue inhomogeneity information within each tissue type. Thus, the CNN can extract and transfer more information from other imaging modalities and better assist the physics-model-based microwave imaging. In the previous work, CNN has been used for the estimation of CT, Positron Emission Tomography (PET) images from MR images[23-25]. However, to the best of our knowledge, it is the first time that CNN is utilized to extract prior information from another imaging modality to assist the inverse scattering based dielectric image reconstruction.

In another aspect, a CNN-assisted multi-modality microwave imaging method is provided. The method is demonstrated to be applicable to brain dielectric imaging using MR to train the CNN.

In another aspect, a method for constructing dialect images in a digital medium environment is provided. The method includes a step of training a convolutional neural network to learn a complex mapping function from patient non-dielectric images to dielectric images at a single frequency or multiple frequencies. Characteristically, the convolutional neural network is trained with a test set derived from characterized images. The trained convolutional neural network is applied to a subject's non-dielectric imaging data to determine an initial predicted dielectric image. Finally, the initial predicted dielectric image is applied as a starting input for a physics-model-based iterative dielectric image reconstruction model to form a final predicted dielectric image where non-dielectric imaging data and initial predicted dielectric image can be at the same spatial resolution or at a different spatial resolution.

In still another aspect, a system for constructing dialect images implementing the methods set forth herein. The system includes a computing device configured to receive a subject's non-dielectric imaging data. The computing device includes a computer processor configured execute a trained convolutional neural network by training an untrained convolutional neural network to learn a complex mapping function from patient non-dielectric images to dielectric images at a single frequency or multiple frequencies to form the trained neural network. The untrained convolutional neural network is trained with a test set derived from characterized images. Characteristically, the computer processor is also configured to apply the trained convolutional neural network to the subject's non-dielectric imaging data to determine an initial predicted dielectric image. Finally, the computer processor is also configured to apply the initial predicted dielectric image as a starting input for a physics-model-based iterative dielectric image reconstruction model to form a final predicted dielectric image where non-dielectric imaging data and initial predicted dielectric image can be at the same spatial resolution or at a different spatial resolution.

BRIEF DESCRIPTION OF THE DRAWINGS

The patent or application file contains at least one drawing executed in color. Copies of this patent or patent application publication with color drawing(s) will be provided by the Office upon request and payment of the necessary fee."

FIGS. 3A, 3B, 3C, 3D, 3E, 3F, 3G, 3H, 3I, 3J, 3K, 3L, 3M, and 3N: Segmented and synthesized dielectric images from MR T2 images. The top row images are from axial view slice 87 of patient AAG, while the bottom row images are from axial view slice 85 of patient ABB. The first column (A) and (H) are their MR T2 images. (B) and (I) are the tissue segmentation results of the two patients, where purple, green, blue, and red represents CSF, white matter, grey matter and tumor region, respectively. The synthesized dielectric images of $\epsilon$ and $\sigma$ at 1.2 GHz are shown in (C) and (J), (D) and (K), respectively. The synthesized wideband Debye model dielectric images of $\epsilon\_\infty$, $\Delta\epsilon$, $\sigma\_d$ are shown in (E) and (L), (F) and (M), (G) and (N), respectively. All images have 1 mm resolution.

FIGS. 12A, 12B, 12C, 12D, 12E, 12F, and 12G: Patient ABB CNN prediction result and true dielectric image generation. (A) is T1 image at 1 mm resolution. (B) to (F) are 4 mm resolution images. (B) is the CNN predicted $\epsilon$ image. (C) is the MR T2 synthesized $\epsilon$ image using the same approach described in Section 2. (D) is the random map to add tissue inhomogeneity to (C). (E) is the true E image generated by multiplying (D) to (E). (F) is the difference image between the synthesized and the CNN predicted E image. (G) is the difference image between the true and CNN predicted E image.

FIGS. 15A, 15B, 15C, 15D, 15E, and 15F: Quantitative analysis of 4 mm resolution reconstruction for patient ABB. First row are analysis of reconstruction from CNN predicted image as background. Second row are analysis of reconstruction from brain phantom filled with average tissue value as background. The first column are the residual errors of the scattered field cost function. The second column are the $P_{err}$ of the reconstructed $\epsilon$ image and its initial background image. The third column are the $P_{err}$ of the reconstructed $\sigma$ image and its initial background image.

FIGS. 16A, 16B, 16C, 16D, 16E, 16F, 16G, 16H, 16I, and 16J: 4 mm resolution single frequency reconstruction results of patient AAB slice 90. The first row are $\epsilon$ images and the second row are $\sigma$ images. First column are the true dielectric images. Second column are CNN predicted dielectric images. Third column are the recovered images starting from CNN predicted image. Fourth column are the recovered images starting from brain phantom filled with average tissue value.

FIGS. 17A, 17B, 17C, 17D, 17E, and 17F: Quantitative analysis of 4 mm resolution reconstruction for patient AAB. First row are analysis of reconstruction from CNN predicted image as background. Second row are analysis of reconstruction from brain phantom filled with average tissue value as background. The first column are the residual errors of the scattered field cost function. The second column are the $P_{err}$ of the reconstructed $\epsilon$ image and its initial background image. The third column are the $P_{err}$ of the reconstructed $\sigma$ image and its initial background image.

FIGS. 20A, 20B, 20C, 20D, 20E, and 20F: Quantitative analysis results of 2 mm resolution reconstruction (FIG. 19). First and second row are the results of 2 mm resolution reconstruction using one and four frequencies respectively. The first column are the scattered field cost function residual errors. The second and the third column are the $P_{err}$ of the predicted and reconstructed $\epsilon$ and $\sigma$ images at 1.2 GHz, respectively.

DETAILED DESCRIPTION

Figure 1A:
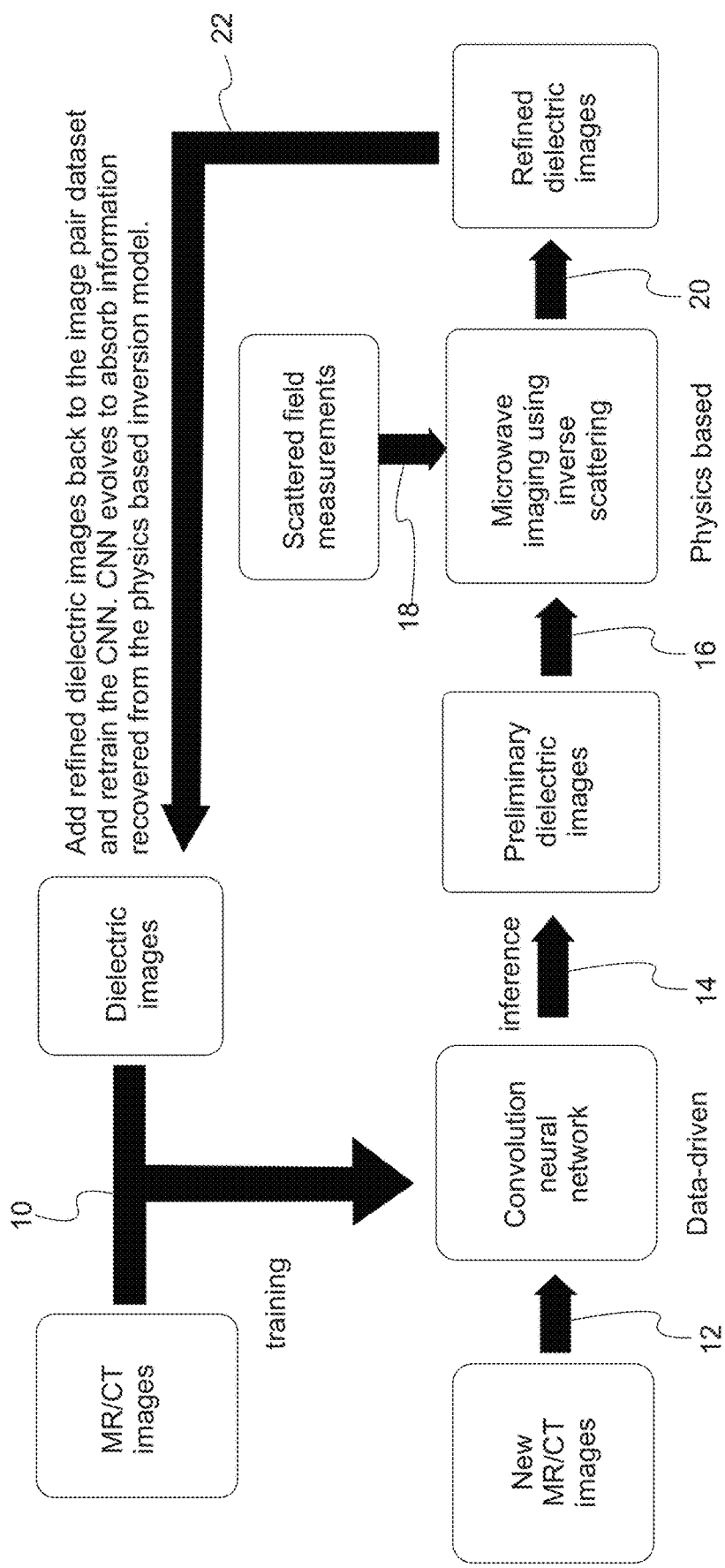
FIG. 1A: CNN assisted multi-modality dielectric imaging method description.

Reference will now be made in detail to presently preferred embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

As used herein, the term "about" means that the amount or value in question may be the specific value designated or some other value in its neighborhood. Generally, the term "about" denoting a certain value is intended to denote a range within +/−5% of the value. As one example, the phrase "about 100" denotes a range of 100+/−5, i.e. the range from 95 to 105. Generally, when the term "about" is used, it can be expected that similar results or effects according to the invention can be obtained within a range of +/−5% of the indicated value.

The term "and/or" means that either all or only one of the elements of said group may be present.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

The phrase "composed of" means "including" or "consisting of." Typically, this phrase is used to denote that an object is formed from a material.

With respect to the terms "comprising," "consisting of," and "consisting essentially of," where one of these three terms is used herein, the presently disclosed and claimed subject matter can include the use of either of the other two terms.

The term "one or more" means "at least one" and the term "at least one" means "one or more." The terms "one or more" and "at least one" include "plurality" as a subset.

The term "substantially," "generally," or "about" may be used herein to describe disclosed or claimed embodiments. The term "substantially" may modify $\sigma$ value or relative characteristic disclosed or claimed in the present disclosure. In such instances, "substantially" may signify that the value or relative characteristic it modifies is within ±0%, 0.1%, 0.5%, 1%, 2%, 3%, 4%, 5% or 10% of the value or relative characteristic.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits. In the specific examples set forth herein, concentrations, temperature, and reaction conditions (e.g. pressure, pH, etc.) can be practiced with plus or minus 50 percent of the values indicated rounded to three significant figures. In a refinement, concentrations, temperature, and reaction conditions (e.g., pressure, pH, etc.) can be practiced with plus or minus 30 percent of the values indicated rounded to three significant figures of the value provided in the examples. In another refinement, concentrations, temperature, and reaction conditions (e.g., pH, etc.) can be practiced with plus or minus 10 percent of the values indicated rounded to three significant figures of the value provided in the examples.

The term "computing device" refers generally to any device that can perform at least one function, including communicating with another computing device. Sometimes the computing device is referred to as a computer.

When a computing device is described as performing an action or method step, it is understood that the computing devices are operable to perform the action or method step typically by executing one or more lines of source code. The actions or method steps can be encoded onto non-transitory memory (e.g., hard drives, optical drive, flash drives, and the like).

The processes, methods, or algorithms disclosed herein can be deliverable to/implemented by a computing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in a software executable object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

The term "neural network" refers to a machine learning model that can be trained with training input to approximate unknown functions. In a refinement, neural networks include a model of interconnected digital neurons that communicate and learn to approximate complex functions and generate outputs based on a plurality of inputs provided to the model.

Throughout this application, where publications are referenced, the disclosures of these publications in their entireties are hereby incorporated by reference into this application to more fully describe the state of the art to which this invention pertains.

With respect to the terms "comprising," "consisting of," and "consisting essentially of," where one of these three terms is used herein, the presently disclosed and claimed subject matter can include the use of either of the other two terms.

Abbreviations:

"CNN" means convolutional neural network.
"CSF" means cerebrospinal fluid.
"CT" means computed tomography.
"MR" means magnetic resonance.
"SPM" means statistical parametric mapping.
"BIM" means born iterative method.
"BRATS" means brain tumor image segmentation benchmark.
"FDTD" means finite-difference time-domain.

Figure 1B:
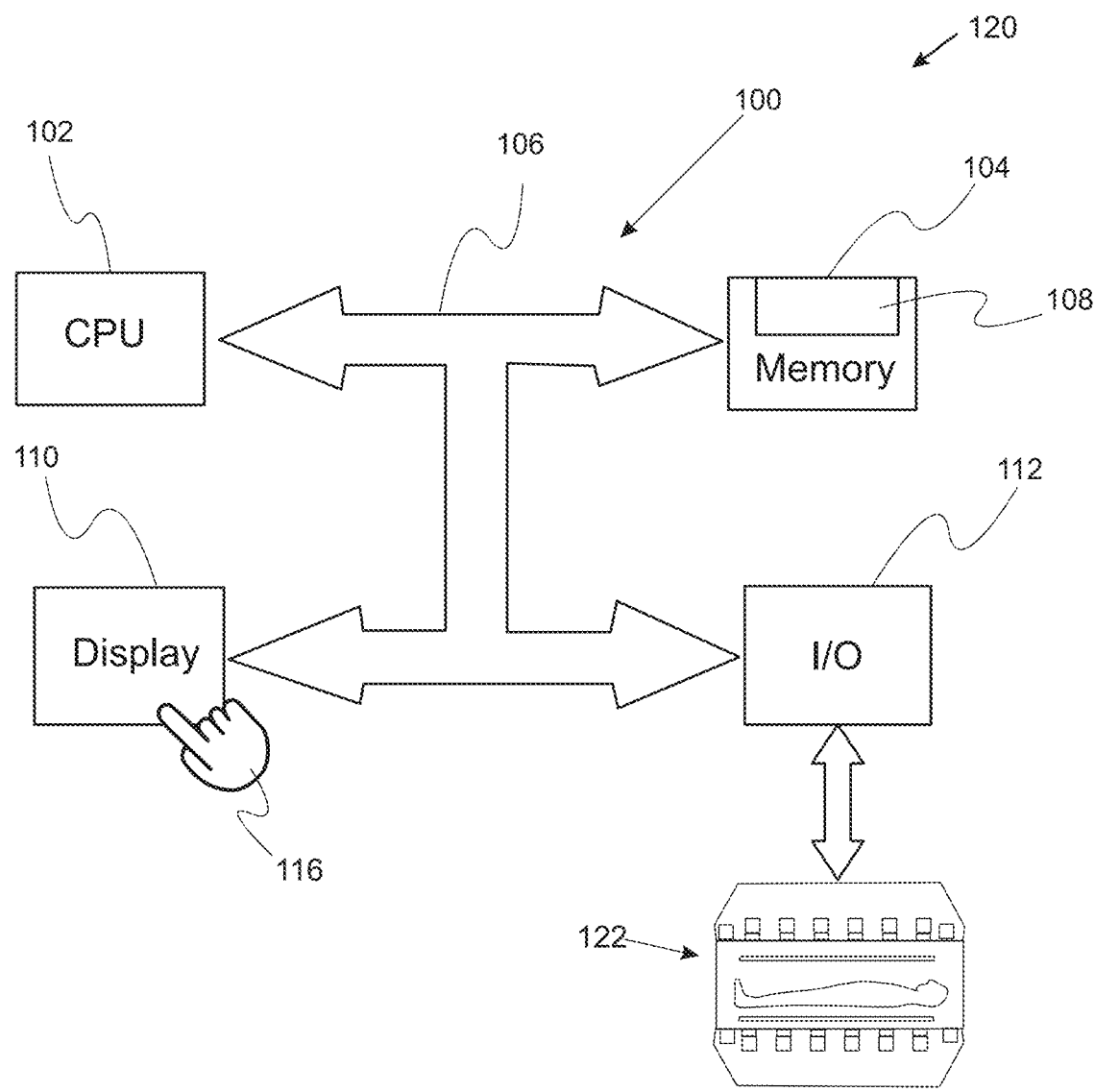
FIG. 1B: Schematic of a computing devices and system for implementing the methods set forth herein.
Figure 10:
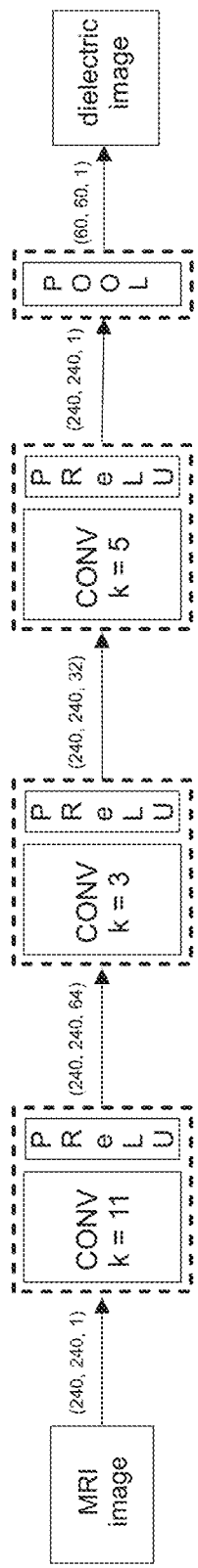
FIG. 10: Block diagram of CNN for learning dielectric image from an MR T1 image. First two values within the bracket on the arrow indicate the size of the image in x and y direction, respectively. The third value indicates number of channels/filters for the layer on the left. K denotes the filter size.
Figure 11:
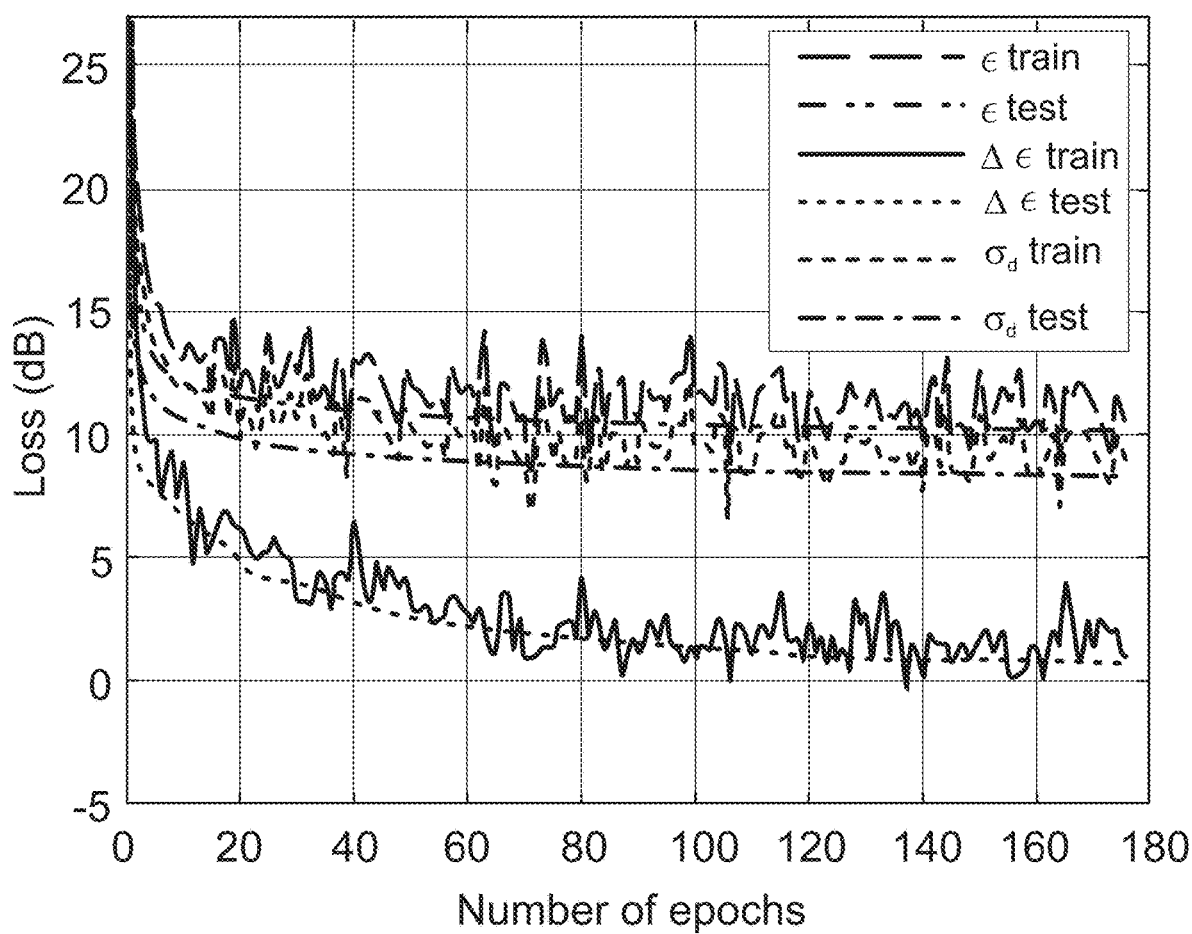
FIG. 11: The cost function value (loss in arbitrary unit) at the end of every epoch for three sets of network learning in the multi-frequency setup.

With reference to FIG. 1, a method for reconstructing dielectric images in a digital medium environment is provided. The method includes steps 10 of training a convolutional neural network to learn a complex mapping function from patient non-dielectric images to dielectric images at a single frequency or multiple frequencies. The convolutional neural network is trained with a test set derived from characterized images (e.g., medical images). Dielectric images are images that display variations in local permittivity and conductivity. In this context, non-dielectric images are images obtained from any technique that provides an image of an object or subject that does not have information of permittivity and conductivity. In other words, the non-dielectric image data is input data. Examples of non-dielectric images includes, but are not limited to magnetic resonance images, computed tomography images, ultrasound images, and combination thereof. A subject's non-dielectric imaging data or test image data is provided as input to the convolutional neural network in step 12. The trained convolutional neural network is applied to a subject's non-dielectric imaging data in step 14 to determine an initial predicted dielectric image. FIG. 10 depicts a convolutions neural network which can include a plurality of convolutional layers and one or more pooling layers. In should be appreciated that the convolutional network can include convolutional layers, pooling layers, fully connected layers, normalization layers, a global mean layer, and a batch-normalization layer.

In a refinement, the CNN is trained in a learning process that can be done iteratively. After generating dielectric images for a certain number of times, the CNN can be retrained with this new set of images for improved prediction.

Advantageously, the initial predicted dielectric image is provided as input to physics-model-based iterative dielectric image reconstruction model in step 16 as a starting input for physics-model-based iterative dielectric image reconstruction model. Scattered field measurements are also provided to the physics-model-based iterative dielectric image reconstruction model as input in step 18 as described below in more detail. In step 20, the physics-model-based iterative dielectric image reconstruction model to the initial predicted dielectric image to form final predicted dielectric image. In this context, the physics-model-based iterative dielectric image reconstruction model has two components: 1) a forward model that relates measurements to the dielectric values, and 2) a reconstruction step, where dielectric values are estimated directly or iteratively from measurements. With respect to the forward model, the physics-model-based iterative dielectric image reconstruction model includes a method of deriving the dielectric function from measurable quantities through equations derived from and/or consistent with Maxwell's equations for continuous media. Examples of such measurable quantities include, but are not limited to, frequency of incident, scattered, reflected, absorbed, or emitted electromagnetic radiation; electric fields at each location in a tissue being studied; magnetic fields at each location in a tissue being studied; the current density (or current) electric fields at each location in a tissue being studied; and the like. With respect to the reconstruction step, the fields (or contrast sources) and the dielectrics are solved sequentially in each iteration to alleviate the nonlinearity as set forth above. In addition, the approaches can use the conjugate gradient method, Tikhonov regularization, and the constraint-based methods such as l1-l2 norm, group sparsity, and shaped. Details of these techniques are found in P. Shah, U. K. Khankhoje, and M. Moghaddam, "Inverse scattering using a joint l1-l2 norm-based regularization," *IEEE Transactions on Antennas and Propagation*, vol. 64, no. 4, pp. 1373-1384, 2016; G. Chen, P. Shah, and M. Moghaddam, "Multi-parameter microwave inverse scattering with group sparsity constraints," in Proc. IEEE Int. Symp. Antennas Propag. USNC/URSI Nat. Radio Sci. Meeting, July 2018, pp. 697-698; and P. Shah and M. Moghaddam, "A fast level set method for multimaterial recovery in microwave imaging," *IEEE Transactions on Antennas and Propagation*, vol. 66, no. 6, pp. 3017-3026, 2018; the entire disclosures of which are hereby incorporated by reference. In a refinement, the physics-model-based iterative dielectric image reconstruction model is a microwave differential inverse scattering algorithm (e.g., a model) as set forth below in more detail. In a refinement, the non-dielectric imaging data and initial predicted dielectric image can be at the same spatial resolution or at a different spatial resolution.

Typically, the test set includes pairs of non-dielectric images and corresponding synthetic dielectric images. In one variation, the corresponding synthetic dielectric images are a set of dielectric images derived from data obtained in a prior imaging study independent of the imaging study (e.g., 3D anatomical imaging, MR, CT, Ultrasound) that used to form the set of non-dielectric images. In a refinement, the corresponding synthesized dielectric images are formed by segmenting imaging data from a prior clinical imaging study into different tissue types and then mapping previously determined corresponding dielectric values for each tissue type as shown in step 20. In this regard, magnetic resonance T1 images are acquired via actual MR scans and a set of corresponding dielectric images is synthesized from the magnetic resonance T1 images or from co-registered images from a different imaging technique (e.g., T2 scans, computerized tomography, or ultrasound). In a further refinement, T2 images are applied for segmentation to get different tissue type regions and map each tissue type being mapped to its measured dielectric values to create the corresponding synthesized dielectric images.

In a variation, the non-dielectric images set forth above are magnetic resonance images, computed tomography images, ultrasound images, and/or combinations thereof. In a refinement, the non-dielectric images are T1 magnetic resonance images or T2 magnetic resonance images.

Advantageously, the non-dielectric images and the corresponding reconstructed dielectric images can be used as an additional set of image pairs to train the convolutional neural network as depicted in step 22.

In another variation, the test set includes pairs of non-dielectric image data and corresponding experimental dielectric image data. In this regard, experimental dielectric image data can be formed by building layered dielectric tissue phantoms with known dielectric values and which have similar dielectric values to those of tissues and then acquiring magnetic resonance images of those dielectric phantoms to create magnetic resonance-dielectric image pairs.

In another embodiment, a computing device implementing the methods set forth herein is provided. In general, computing devices are computer processor-based electronic devices. With reference to FIG. 1C, computing device 100 includes computer processor 102 that executes the instructions for authoring the chemical mechanism problem or solving it. It should be appreciated that virtually any type of computer processor may be used, including microprocessors, multi-core processors, and the like. The instructions for the method typically are stored in computer memory 104 and accessed by computer processor 102 via connection system 106. In a variation, connection system 106 is and/or includes a data bus. In a refinement, computer memory 104 includes a computer-readable medium 108 which can be any non-transitory (e.g., tangible) medium that participates in providing data that may be read by a computer. Specific examples for computer memory 104 include, but are not limited to, random access memory (RAM), read-only memory (ROM), hard drives, optical drives, removable media (e.g., compact disks (CDs), DVD, flash drives, memory cards, etc.), and the like, and combinations thereof. In another refinement, computer processor 102 receives instructions from computer memory 104 and executes these instructions, thereby performing one or more processes, including one or more of the processes described herein. Computer-executable instructions for implementing the imaging methods may be compiled or interpreted from computer programs created using a variety of programming languages and/or technologies including, without limitation, and either alone or in combination, Java, C, C++, C#, Fortran, Pascal, Visual Basic, Java Script, Perl, PL/SQL, etc.

Display 110 is also in communication with computer processor 102 via connection system 176. Computing device 100 also includes various in/out ports 112 through which data from a pointing device 114 may be accessed by computer processor 102. Examples for the computing device include, but are not limited to, desktop computers, laptops, or servers. Examples of pointing devices include a mouse, touch screen, stylus, trackball, joystick or touchpad. In a particularly useful variation, the pointing device is incorporated into display 110 as a touch screen by which user 116 interacts with a finger. In a variation, a non-transitory storage medium or media (hard drives, optical drives, removable media (e.g., compact disks (CDs), DVD, flash drives, memory cards, etc.) has encoded thereon instructions for the steps executed by computer processor 102 in performing the steps of the methods set forth herein. For example, computing device 100 is configured to receive a subject's non-dielectric imaging data. Computer processor 102 is configured execute a trained neural network by training an untrained convolutional neural network to learn a complex mapping function from patient non-dielectric images to dielectric images at a single frequency or multiple frequencies to form the trained neural network. In a refinement, the single frequency or each of the multiple frequencies are in the range from 0.2 GHz to 4 GHz. In another refinement, the single frequency or each of the multiple frequencies are in the range from 0.5 GHz to 2 GHz. Characteristically, the untrained convolutional neural network being trained with a test set derived from characterized images. The computer processor is also configured to apply the trained convolutional neural network to a subject's non-dielectric imaging data to determine an initial predicted dielectric image. Computer processor 102 is further configured to apply the initial predicted dielectric image as a starting input for a physics-model-based iterative dielectric image reconstruction model to form a final predicted dielectric image where non-dielectric imaging data and initial predicted dielectric image can be at the same spatial resolution or at a different spatial resolution. The final predicted dielectric image can be rendered on display 116 and/or stored in computer memory 104 including computer-readable medium 108.

In a variation, an imaging system 120 includes computing device 100 and one or more medical imaging devices 122 to collect non-dielectric imaging data from a subject to determine an initial predicted dielectric image. Examples of the one or more medical imaging devices include, but are not limited to, magnetic resonance images, computed tomography images, ultrasound images, and/or combinations thereof. Moreover, each of the details of the methods set forth herein are applicable to the imaging system.

Additional details of the present invention are set forth below in G. Chen, P. Shah, J. Stang and M. Moghaddam, "Learning-Assisted Multimodality Dielectric Imaging," in IEEE Transactions on Antennas and Propagation, vol. 68, no. 3, pp. 2356-2369, March 2020; the entire disclosure of which is hereby incorporated by reference in its entirety.

The following examples illustrate the various embodiments of the present invention. Those skilled in the art will recognize many variations that are within the spirit of the present invention and scope of the claims.

1. Overview of CNN-Assisted Multi-Modality Microwave Imaging Method

1.1 Method Overview

To overcome the non-uniqueness, ill-posedness, and non-linearity issues of microwave dielectric imaging, a CNN-based multi-modality imaging method, which effectively and efficiently incorporates information acquired from other imaging modalities (e.g., MR, CT and Ultrasound) into the dielectric image reconstruction process is developed. To train the CNN, a synthetic approach to generate synthetic dielectric images is provided. For example of the brain, images from another modality are used, and then MR/CT/Ultrasound and synthetic dielectric image pairs are created for training. Those image pairs can also be generated through an experimental approach, which will be discussed later. In either case, the CNN learns the complex nonlinear mapping function from MR/CT/Ultrasound brain images to dielectric images. Then, for each new patient, the CNN can take in their MR/CT/Ultrasound images and produce predicted dielectric images. Those images are subsequently used as the starting point for dielectric reconstruction with a model-based microwave imaging method. Because the CNN-predicted dielectric images contain the abundant brain structure and pixel-level tissue property information transferred from other imaging modalities, they are much closer to the true dielectric images compared to traditional initialization methods. By starting from the CNN-predicted dielectric image, the computational electromagnetic forward model produces a much more accurate initial estimate of the total electric field, which significantly reduces the nonlinearity and ill-posedness of the microwave imaging problem. Then, by performing physics-model-based microwave imaging, additional information that may have been missing from the training data and therefore not learned by the CNN is potentially recovered by the physics-based inverse scattering model. Finally, the reconstructed dielectric image and its corresponding MR/CT/Ultrasound image is used as a new set of image pairs in our training database and update the training of the CNN. In this way, the CNN model dynamically evolves to absorb the new information recovered from the physics-based model and improves its capability to infer more accurate dielectric images from future MR/CT/ultrasound images. The flow of the complete multi-modality microwave dielectric imaging process is shown in FIG. 1. In the present example, MR is used as the prior modality throughout to demonstrate this learning-assisted, physics-based multi-modality dielectric imaging method. Further, we use the human brain as the case study for demonstrating the proposed method. Specifically, a CNN is developed which can take in an MR T1 image of a brain and produce a predicted dielectric image, and then the Born Iterative Method (BIM) [26] is applied in the physics-based image refinement step.

1.2 Acquiring Training Data for CNN

For the brain dielectric imaging problem, the key to training the CNN is having enough MR and dielectric brain image pairs. These image pairs can be acquired either synthetically or experimentally. In the synthetic approach, the brain MR T1 images are acquired via actual MR scans, and a set of corresponding dielectric images is synthesized from those MR T1 images or from co-registered images from a different imaging study (such as MR T2, CT, or ultrasound) of the same brain. To synthesize the dielectric images, those MR/CT/Ultrasound images are first segmented into different brain tissue types and then mapped to their corresponding dielectric values from prior studies of human tissue dielectrics[27]. Alternatively, in the experimental approach, dielectric brain phantoms are built with materials of similar dielectric values to brain tissues. MR images of those dielectric brain phantoms are then acquired to create the MR-dielectric image pairs. The advantage of the synthetic approach is that the derived dielectric brain images contain accurate structural information of the brain. However, the pixel-level dielectric value in these synthetic images may not be very accurate, as they are estimated based on several tissue types and their expected dielectric values. On the other hand, in the experimental approach, we obtain highly accurate dielectric values as well as their corresponding raw MR T1 and T2 values in the constructed dielectric phantom. However, the structure of these brain phantoms may be a poor approximation of a real brain due to the difficulty in constructing such complex phantoms. As the CNN can learn both the structure-mapping and the nonlinear pixel-value-mapping relationship between the MR and dielectric images, it would be ideal to have both synthetically and experimentally generated MR-dielectric image pairs for training. Embodiments of the present invention focus on generating and using synthetic image pairs for training.

1.3 Simulation Study of the Proposed Method

Figure 2:
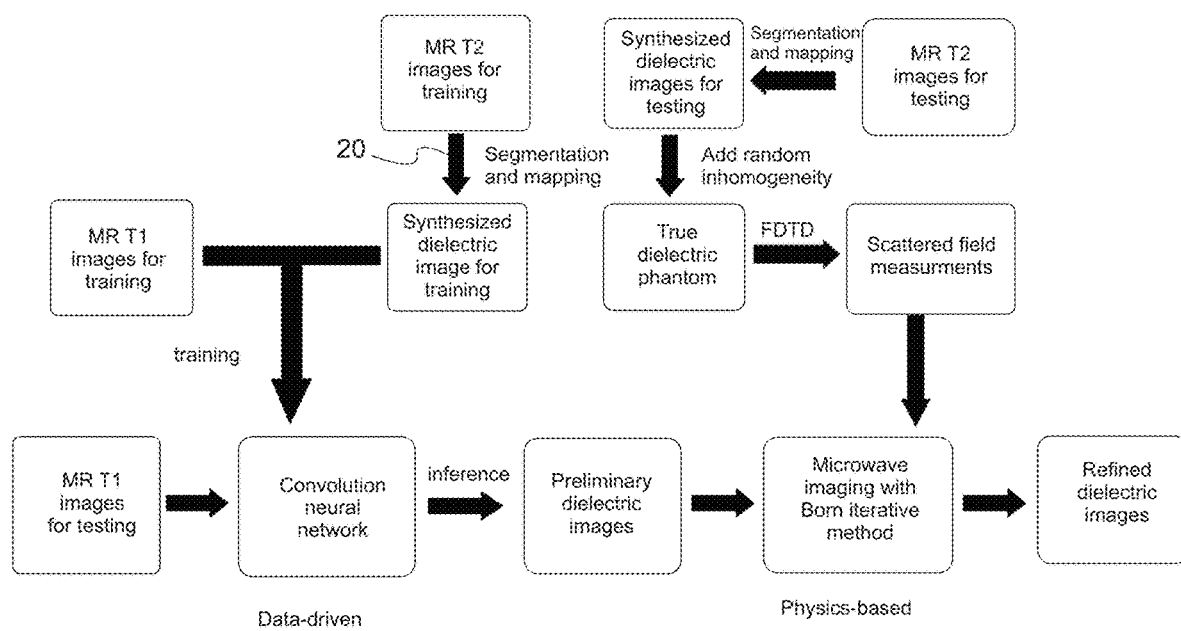
FIG. 2: Simulation flow to evaluate the CNN assisted multi-modality dielectric imaging method. The light green block are images used for training the CNN. The light blue block are images used during the testing phase of the learning assisted imaging method.
Figure 4A:
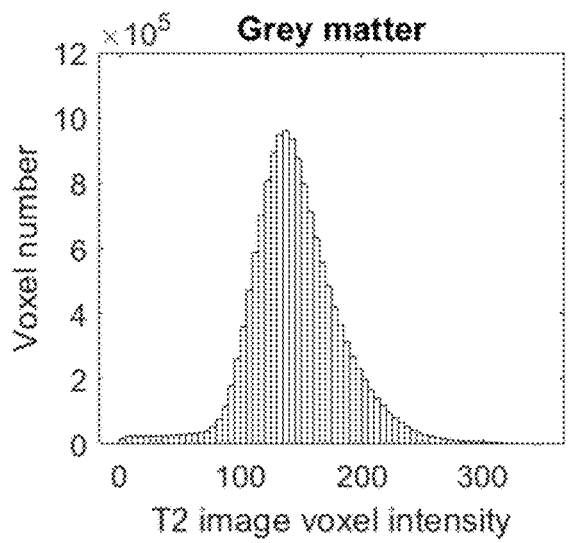
FIGS. 4A, 4B, 4C, and 4D: T2 pixel value histogram for different tissue types. We fit the T2 image voxel histogram of each tissue type with a Gaussian distribution model, where the fitted Gaussian probability density functions (PDF) are plotted in FIG. 5. The mean $\mu\_T2$ and the standard deviation $\delta\_T2$ of each brain tissue type are shown in Table 1.
Figure 4B:
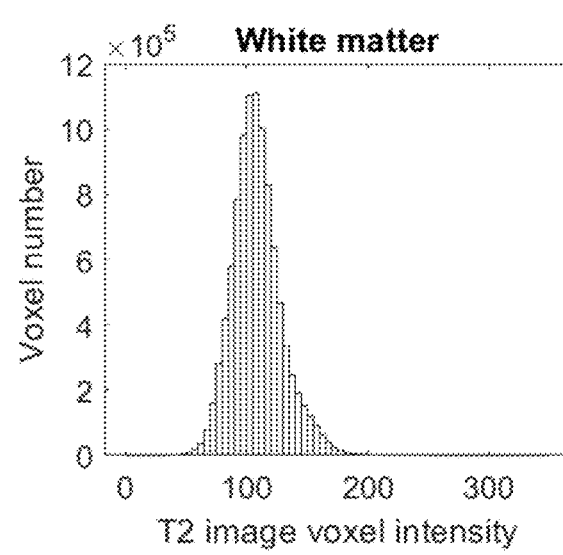
Figure 4C:
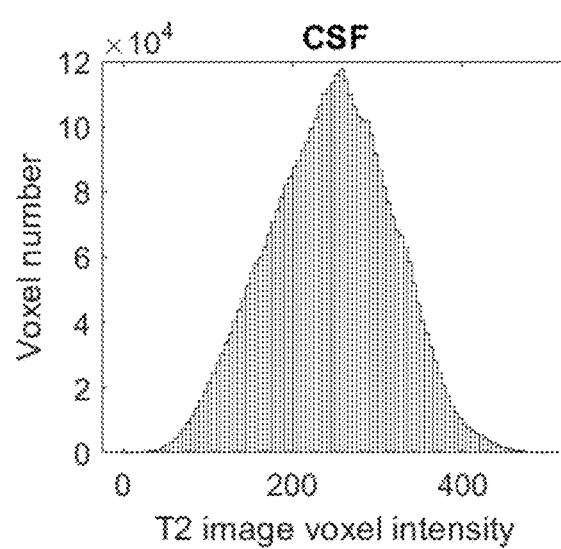
Figure 4D:
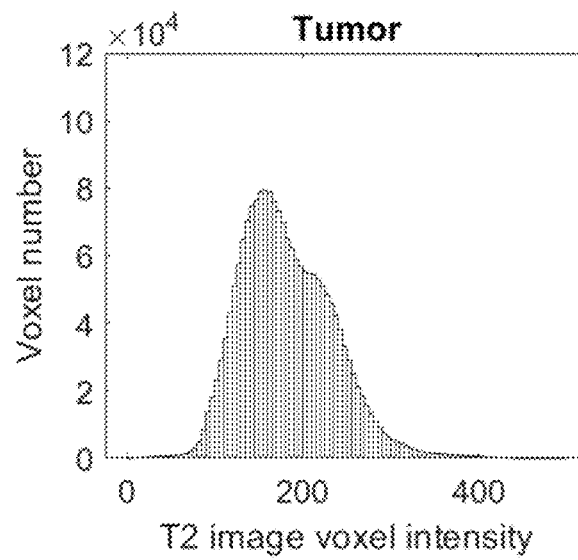
Figure 5:
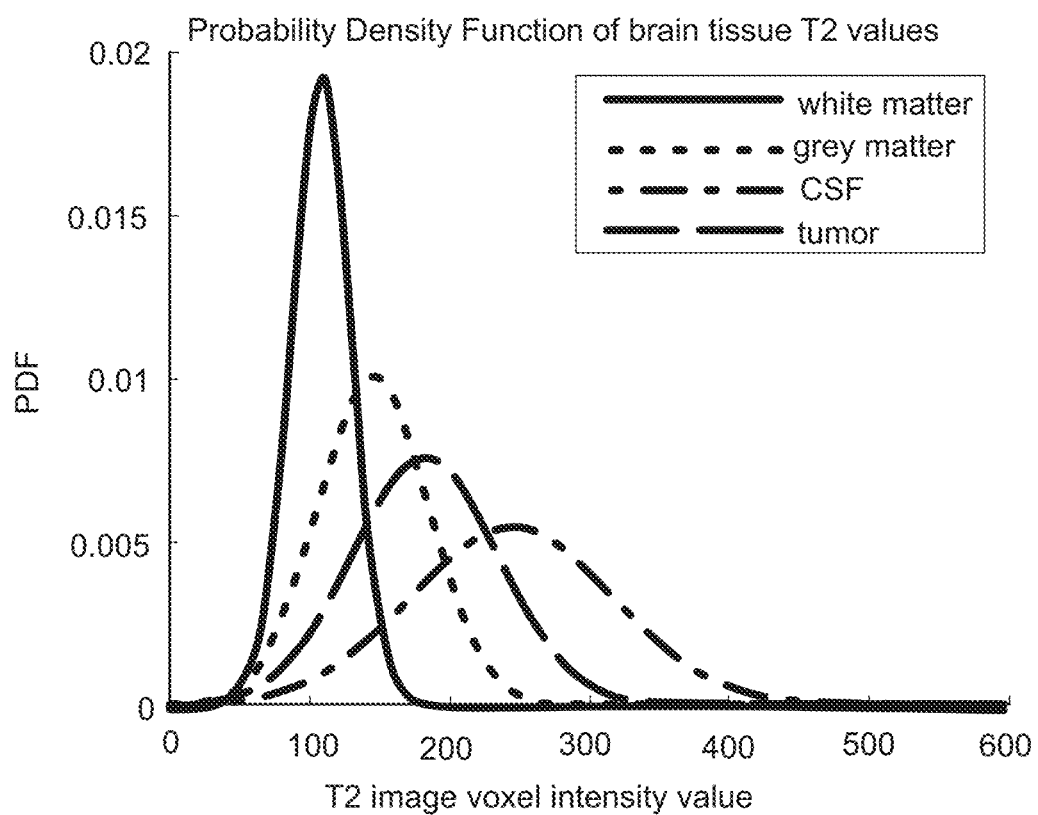
FIG. 5: Gaussian model fitted PDF of each tissue type.

A simulation study as depicted in FIG. 2 is performed to evaluate the proposed method. To create the MR-dielectric image pairs for training the CNN and testing the proposed imaging method, the MR image dataset from the Brain Tumor Image Segmentation Benchmark (BRATS) [28] is used. The BRATS dataset contains co-registered MR T1 and T2 images of many brain cancer patients. The T2 image is used for segmentation to get different brain tissue type regions and map each tissue type to their measured dielectric values to create synthesized dielectric images. Then a subset of the T1 and the synthesized dielectric images are used for training the CNN (shown as light green block in FIG. 2), while the rest of them are reserved for testing the complete imaging method (shown as blue block in FIG. 2). It is important to note that: though normally the T1 images can also be used to synthesize the dielectric images, the T1 images in these experiments are insulated from the dielectric image synthesizing process thereby avoiding the situation where it is only demonstrated that CNN can be used to learn the process of synthesizing dielectric images from MR images. Moreover, as there is no explicit function to map an MR T1 image to an MR T2 image, the capability of the CNN to map a T1 image to a T2 synthesized dielectric image is non-trivial. As shown in FIG. 2, during the training phase, a subset of the T1-dielectric image pairs are used to train the CNN. During the testing phase, the remaining T1 images are fed to the CNN to generate predicted dielectric images, while the remaining synthesized dielectric images are used to create the estimated true dielectric phantom with added random inhomogeneity (to be discussed in Section 4.1), which are used to generate realistic scattered field measurement data. Then the scattered field, predicted preliminary dielectric images and the model-based inverse scattering method will produce the refined dielectric images.

2 Generate Synthetic MR Dielectric Image Pairs

To create the MR-dielectric image pairs, we will discuss the two key steps in synthesizing the dielectric images: A. image segmentation, and B. tissue dielectric value mapping.

2.1 Image Segmentation

Segmentation is performed on the MR T2 images from the BRATS dataset. The skull and skin of all T1 and T2 images in BRATS are already stripped to guarantee patient anonymity [28], leaving four major tissue types in the T2 images: white matter, grey matter, cerebrospinal fluid (CSF) and glioma tumor. To segment the images, the unified segmentation method [29] implemented in the Statistical Parametric Mapping (SPM) tool box [30] is used. The unified segmentation method derives a model based on a mixture of Gaussian distributions and incorporates a smooth and non-linear registration with tissue probability maps. The SPM toolbox combines field bias correction, spatial normalization, and segmentation into a single model. The SPM toolbox is used to segment the T2 images and generate probability maps of the white matter, grey matter, CSF and the background. Then each pixel in the T2 image is assigned to the tissue type which has the highest probability. As the BRATS dataset provides the true location of the tumor verified by the physician, the T2 images are further segmented by superimposing the region of glioma tumor. In FIGS. 3 (B) and (C), we demonstrate the segmentation result of patient ABB and patient AAG from BRATS dataset. In the segmented image, green, blue, purple, red, and yellow represent the region of white matter, grey matter, CSF, glioma, and the background, respectively. As can be seen, the segmentation results are visually faithful to what the T2 image shows for different tissue regions.

2.2 Tissue Value Mapping

After generating the segmentation map of the patient's T2 image, the synthetic dielectric images is created with those segmentation maps and the measured dielectric values of different brain tissue types. To transfer the inhomogeneity information within each tissue type from the MR T2 image to the synthesized dielectric image, an approach similar to the one described in [31] is used in which MR images are used to synthesize breast dielectric phantoms. Based on the assumptions in [31] that (1) for each tissue type, both its T2 image voxel values and the dielectric image voxel values are clustered, and (2) for each tissue type, the statistical distribution of the T2 voxel value and the dielectric value should be similar, a piecewise-linear mapping method can be used to map the T2 image voxel intensity to the dielectric value for each tissue type. To find the statistical distribution of each tissue type, the T2 image voxels of 20 patients are grouped together according to the four tissue types in the segmentation map: white matter, grey matter, CSF and tumor, and then plot their histogram. As shown in the FIG. 4, the T2 image voxel values of each tissue type are close to Gaussian distributions.

TABLE 1

T2 voxel intensity distribution and the measured dielectric value (at 1.2 GHz) of brain tissue

|  | $\mu_{T2}$ | $\delta_{T2}$ | $\epsilon_m$ | $\sigma_m$ |
| --- | --- | --- | --- | --- |
| white matter | 108.82 | 20.68 | 38.07 | 0.69 |
| grey matter | 145.64 | 39.41 | 51.56 | 1.08 |

TABLE 1-continued

T2 voxel intensity distribution and the measured dielectric value (at 1.2 GHz) of brain tissue

|  | $\mu_{T2}$ | $\delta_{T2}$ | $\epsilon_m$ | $\sigma_m$ |
| --- | --- | --- | --- | --- |
| CSF | 244.62 | 72.72 | 68.09 | 2.55 |
| tumor | 182.24 | 52.25 | N/A | N/A |

The dielectric values of brain tissues were measured from 10 Hz to 20 GHz in [27]. A four-pole Cole-Cole complex dielectric model, shown in (1), was used to fit the measured dielectric values and model their wideband dispersive properties. The parameters of the four-pole Cole-Cole model can be found in [27].

$$\chi_c(\omega) = \epsilon_\infty + \Sigma_{n=1}^4 \frac{\Delta\epsilon_n}{1+(j\omega\tau_n)^{(1-\alpha_n)}} + \frac{\sigma_c}{j\omega\epsilon_0} \quad (1)$$

The capability of the proposed method to reconstruct dielectric images at 4 mm and 2 mm resolution is investigated. For a 4 mm resolution reconstruction, only a single frequency microwave signal at 1.2 GHz is used for image reconstruction, and the tissue property can be represented by the basic dielectric model below.

$$\chi(\omega) = \epsilon + \frac{\sigma}{j\omega\epsilon_0} \quad (2)$$

Figure 6A:
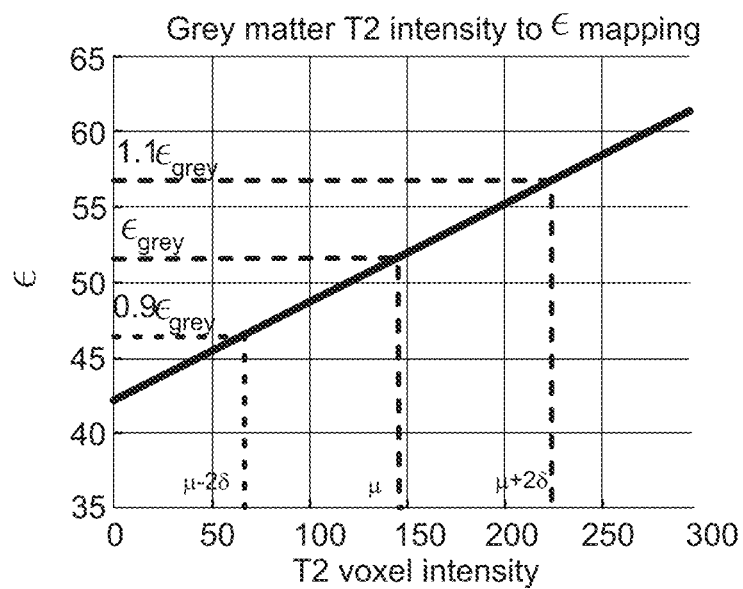
FIGS. 6A and 6B: Grey matter mapping function from T2 image pixel intensity to $\epsilon$ value (A) and $\sigma$ value (B)
Figure 6B:
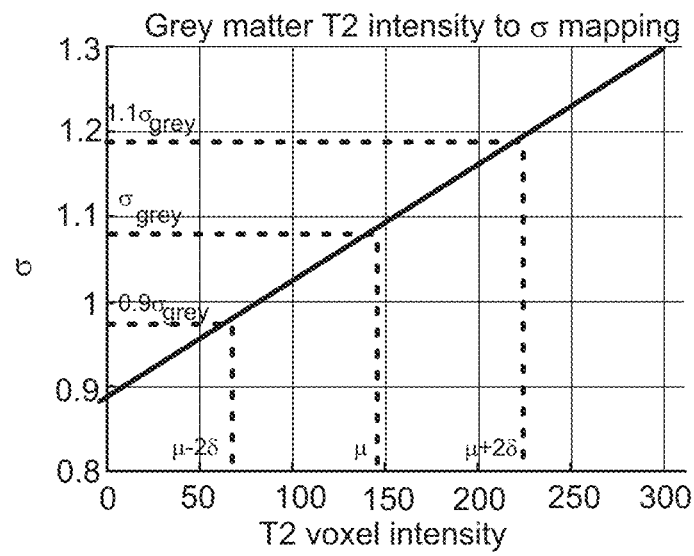

Extracting the basic dielectric model parameters from the four-pole Cole-Cole model in [27], the measured permittivity $\epsilon_m$ and conductivity $\sigma_m$ at 1.2 GHz of each brain tissue types are listed in Table 1. The spread of the measured dielectric values were quantified in [27] to be within a ±10% range. With the assumption that the statistical distribution of the dielectric values and the T2 pixel values of each brain tissue type should fit in a similar Gaussian distribution, we create a piece-wise linear mapping function to map the dielectric values with a range of +10% of the measured values to the T2 pixel intensity values with a range of $\mu_{T2} \pm 2\delta_{T2}$ values. For example, the $\mu_{T2} - 2\delta_{T2}$ T2 value is mapped to the $0.9\epsilon_m$ and $0.9\sigma_m$ values, and $\mu_{T2} + 2\delta_{T2}$ T2 value is mapped to the $1.1\epsilon_m$ and $1.1\sigma_m$ values. The linear mapping functions we created are shown in (3) and (4) below, $$\epsilon(i) = 1.1\epsilon_m + \frac{(0.9\epsilon_m - 1.1\epsilon_m) \times [V_{T2}(i) - (\mu_{T2} + 2\delta_{T2})]}{(\mu_{T2} - 2\delta_{T2}) - (\mu_{T2} + 2\delta_{T2})} \quad (3)$$

$$\sigma(i) = 1.1\sigma_m + \frac{(0.9\sigma_m - 1.1\sigma_m) \times [V_{T2}(i) - (\mu_{T2} + 2\delta_{T2})]}{(\mu_{T2} - 2\delta_{T2}) - (\mu_{T2} + 2\delta_{T2})} \quad (4)$$

where $V_{T2}$ is the T2 image pixel value and i is the index of the pixel. As there are no studies of the brain tumor dielectric values in our desired frequency range, we use the conclusion from [32] that the dielectric values of the brain tumors are roughly 30% higher than the surrounding tissues due to their higher water content, and map the tumor region T2 values to the most probable non-tumor brain tissue in the segmentation map and increase the mapped dielectric values by 30%. As an example of mapping the T2 to dielectric values, the final linear mapping function between T2 value and dielectric value of grey matter is shown in FIG. 6. After mapping the 1 mm resolution T2 image to the 1 mm resolution dielectric image at 1.2 GHz, we down-sample the dielectric image to 4 mm resolution using bi-linear interpolation. As an example, the synthesized 1 mm resolution dielectric images for patient AAG and patient ABB are shown in FIG. 3. The downsampled 4 mm resolution 1.2 GHz synthetic dielectric images of patient AAG created for training are in FIG. 7 (B),(C).

Figure 8A:
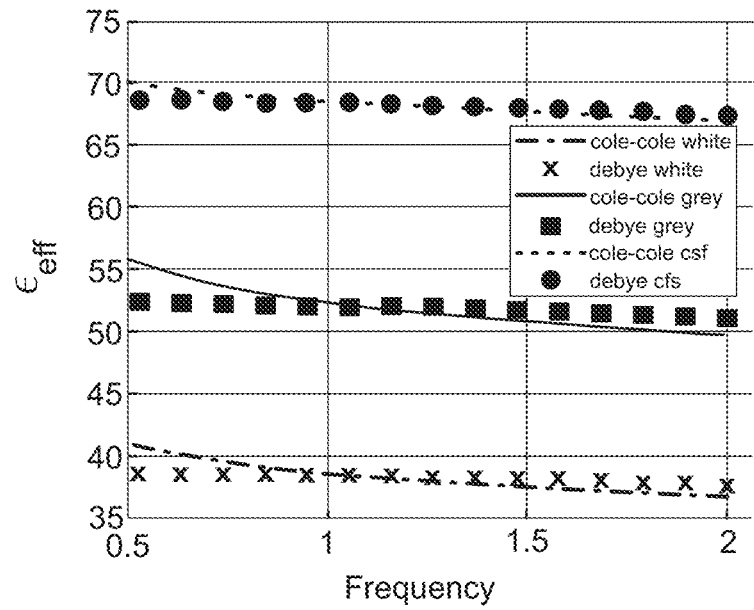
FIGS. 8A and 8B: Results of fitting single-pole Debye model to four-pole Cole-Cole model from 0.5 to 2 GHz.
Figure 8B:
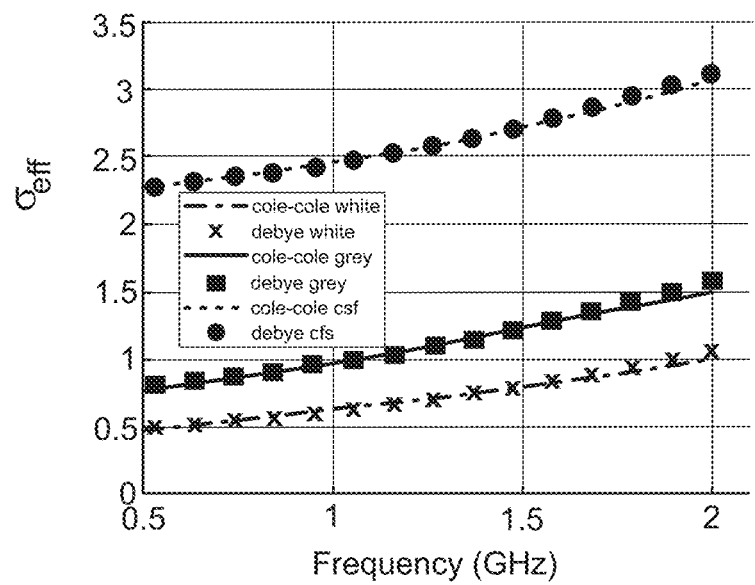

When reconstructing the dielectric images at 2 mm resolution, it is desirable to test the image reconstruction using single and multiple frequencies. As reconstructing a 2 mm resolution image requires solving more unknowns compared to 4 mm resolution, more measurements will likely be useful. However, by increasing the number of frequencies, the dispersive properties of the tissues must be considered. A frequency range of 0.5 GHz to 2 GHz for microwave measurements is chosen due to the constraints of penetration depth and the desired resolution. To consider the dispersion effects of brain tissue in this frequency range while limiting the number of dispersion model parameters for reconstruction, a single-pole Debye model is used to fit the original four-pole Cole-Cole model and the simplex method is used to minimize the cost function shown in (6). Within the Debye model, the three tissue types are restricted to share the same relaxation time $T_d$, while they can have different $\epsilon_\infty$, $\Delta\epsilon$. and $\sigma_d$. The comparison of permittivity and conductivity values from 0.5 GHz to 2 GHz of the fitted Debye model and the original Cole-Cole model is shown in FIG. 8. The $\epsilon_\infty$, $\Delta\epsilon$, and $\sigma_d$ values of the fitted Debye model with different tissue types are shown in Table 2.

$$\chi_d(\omega) = \epsilon_\infty + \frac{\Delta\varepsilon}{1+(j\omega\tau_d)} + \frac{\sigma_d}{j\omega\epsilon_0} \quad (5)$$

$$F = \sum_{i=1}^{N} \|\chi_d^{wm}(\omega_i) - \chi_c^{wm}(\omega_i)\|_2 + \sum_{i=1}^{N} \|\chi_d^{gm}(\omega_i) - \chi_c^{gm}(\omega_i)\|_2 + \sum_{i=1}^{N} \|\chi_d^{csf}(\omega_i) - \chi_c^{csf}(\omega_i)\|_2 \quad (6)$$

TABLE 2

Brain tissue T2 voxel intensity distribution and 0.5-2 GHz Debye model dielectric parameters ($\tau_d$ = 13.27 ps)

| | $\mu_{T2}$ | $\delta_{T2}$ | $\epsilon_\infty$ | $\Delta\epsilon$ | $\sigma_d$ |
|---|---|---|---|---|---|
| white matter | 108.82 | 20.68 | 5.04 | 33.57 | 0.45 |
| grey matter | 145.64 | 39.41 | 5.72 | 46.63 | 0.75 |
| CSF | 244.62 | 72.72 | 18.73 | 50 | 2.22 |

Figures 7A, 7B, 7C:
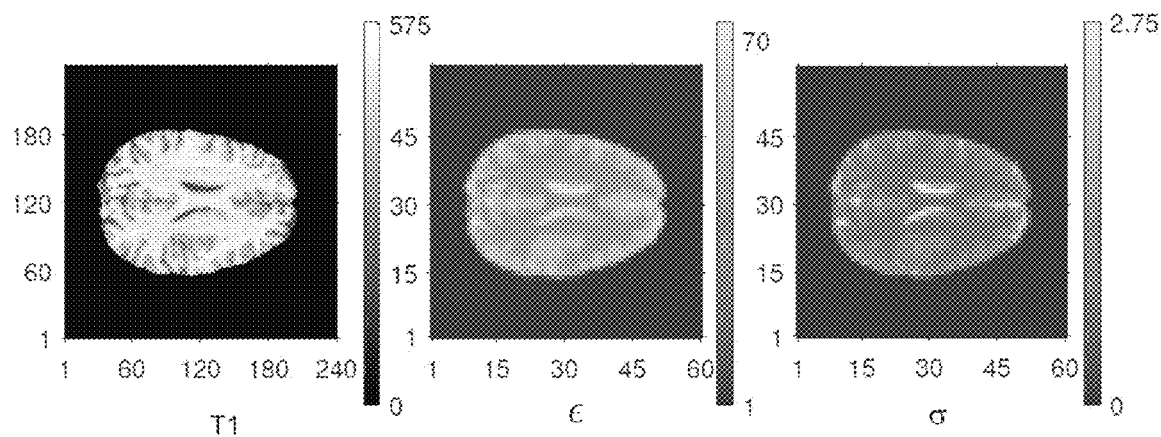
FIGS. 7A, 7B, 7C, 7D, 7E, and 7F: Sample MR T1 and synthesized dielectric image pairs used for training. The sample image pairs are from patient AAG slice 87. The vertical and horizontal axis in each image shows the pixel numbers. (A) T1 image has 1 mm resolution. (B) $\epsilon$ and (C) $\sigma$ images are of 4 mm resolution. (D) $\epsilon\_\infty$, (E) $\Delta\epsilon$, and (F) $\delta\_d$ images are of 2 mm resolution. The MR T1 image and each dielectric image on the right form an image pair to train five CNNs for mapping T1 image to each type of dielectric image for future patients.
Figures 7D, 7E, 7F:
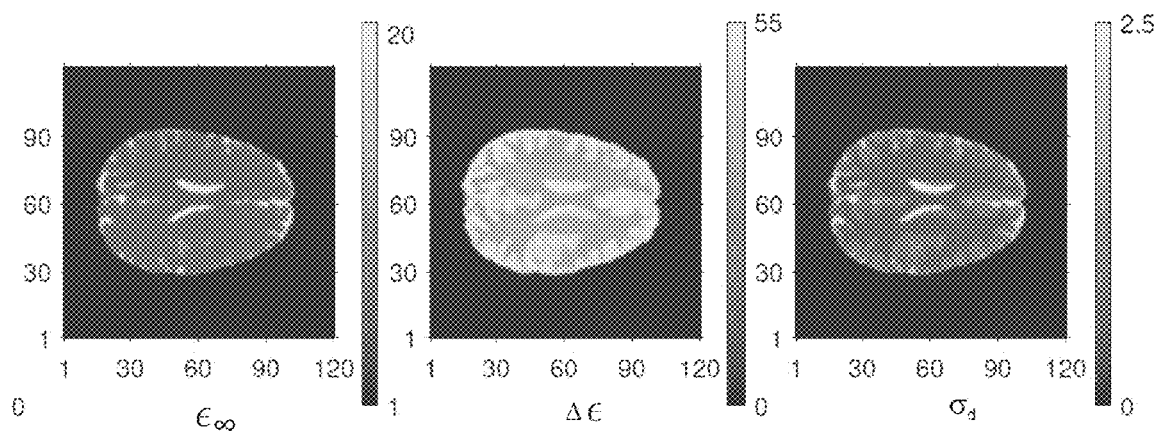

After finding the parameters of the single-pole Debye model for different brain tissue types, the same method in the single frequency case is used to create the piece-wise linear mapping from T2 voxel intensity to the Debye dielectric parameters. The 1 mm resolution MR T2 image is then mapped to the corresponding $\epsilon_\infty$, $\Delta\epsilon$, and $\sigma_d$ Debye parameter images, and downsample those images to 2 mm resolution with bilinear sampling method. As an example, the synthesized 1 mm resolution Debye dielectric images of patient ABB and AAG are shown in FIG. 3. The downsampled 2 mm resolution Debye dielectric images of patient AAG for CNN training are shown in FIG. 7.

3. CNN Architecture and Training

Figure 9:
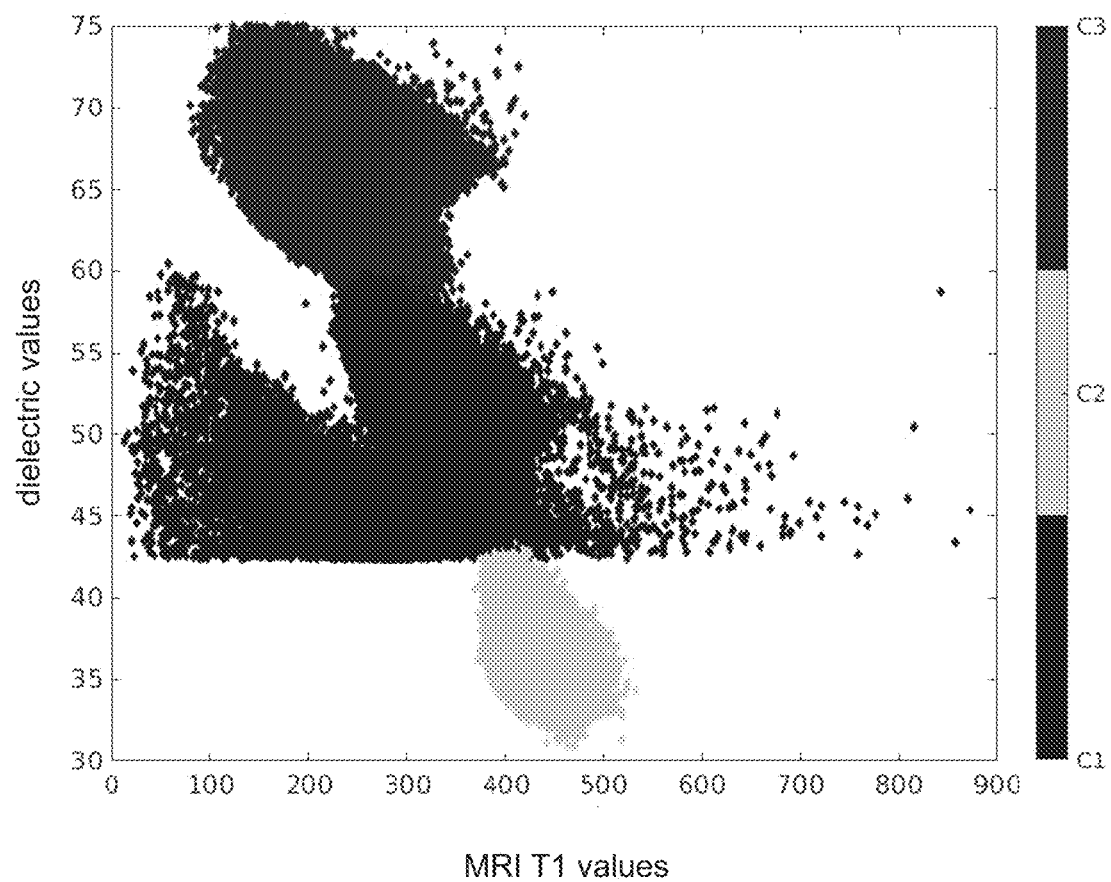
FIG. 9: Relationship between T1 values and $\epsilon$ values of the synthesized dielectric image. In Color bar C1 represents grey matter, C2 represents white matter, and C3 represents CSF. See text for details.

Using the database of MR T1 and synthesized dielectric image pairs, a Convolutional Neural Network (CNN) capable of generating a predicted dielectric image from a given MR T1 image is trained. A CNN is chosen due to its strength in retaining local shape and structure information (since different tissue types should have similar structures in MR and dielectric images) as well as its capability to learn the nonlinear relationship between individual pixel values (MR relaxation time and dielectric). An example of the nonlinear relationship between MR T1 values and dielectric values is shown in FIG. 9, where the values are taken from a single MR T1 image and synthesized dielectric image at 1 mm resolution. As can be seen, grey matter, white matter, and CSF have large variance along both axes and one-many mapping. Fitting a regression curve, which aims to incorporate this large mapping variations from MR T1 values to dielectric values will be very ineffective.

Learning by CNN consists of two stages: training and testing. During the training of CNN, MR T1 images and synthesized dielectric images are used to minimize the cost function of CNN, whereas during the testing phase, an MR T1 image is used to generate the predicted dielectric image. 20 patients from the BRATS dataset are used for our study in this paper. Out of 20 patients' image volumes, 16 volumes are used for training and validation. For each of these 16 volumes, 5% of slices are randomly selected and kept aside for validation. The remaining 4 volumes are used for testing.

Due to the trade-off between penetration depth and resolution, dielectric images generated through inverse scattering at best have spatial resolution in the millimeter range, which is often lower than the spatial resolution of MR T1 images. To use the available information in MR T1 images for learning, the CNN architecture is defined such that the output of the CNN can be at a different spatial resolution than the input of the CNN. The input MR T1 image is at 1 mm spatial resolution, whereas the two spatial resolution cases considered for the predicted dielectric image are at 4 mm and 2 mm. Structure-wise, the CNN architecture is inspired from the structure in [33], though in that work the authors solve a super-resolution problem at the same spatial resolution. Our CNN consists of three stacks of convolution layer (Cony) plus parameterized rectified linear unit (Prelu) and a pooling layer at the end (see FIG. 10). The convolution layer computes the inner product between the local patch of the input image and the kernel whose weights are to be learned. The parameterized rectified linear unit applies nonlinearity through $\max(0,x_i)+\alpha_i \min(0,x_i)$, where $x_i$ is the input to Prelu and $\alpha_i$ is the parameter to be learned. The stack of Conv-Prelu layers learn the local features at the original resolution of T1 image. The pooling layer downsamples the image to a desired resolution by picking the maximum value within the local patch. The rationale behind this architecture is as follows: the Conv-Prelu layers' filter can estimate the non-linear relationship by using the neighbourhood information. Downsampling is kept as an integrated part of the CNN architecture to have the end-to-end learning of mapping a high-resolution MR image to a low-resolution dielectric image, which can further improve the learning results.

For the training, we consider patch-based learning, as our interest is in local transformation from MR T1 to dielectric. Two training dataset are created to map MR T1 images at 1 mm to the dielectric images at 4 mm and 2 mm. For training at 4 mm, two training dataset, MR T1-$\epsilon$; and MR T1-$\sigma$, image pairs are created. For training at 2 mm, three training dataset: MR T1-$\epsilon_\infty$, MR T1-$\Delta\epsilon$, and MR T1-$\sigma_d$ image pairs are created. The 4 mm training dataset are created by selecting a patch of size 80×80 from each 2D axial slice of MR T1 image, moving in a raster scanned manner: left to right and top to bottom with an overlapping of 16 pixels in each direction. The corresponding patch from the synthesized $\epsilon$ and $\sigma$ image of size 16×16 is selected for the respective training dataset. The extra size in the MR T1 image, 80−4×16=16, is considered to handle boundaries for the convolution process. The raster scanning process is repeated for all training images of the database. For 2 mm dataset, the same procedure is repeated with the synthesized Debye model dielectric images ($\epsilon_\infty$, $\Delta\epsilon$, and $\sigma_d$ in Debye model), each of which has a patch size of 32×32.

The cost function L(θ) is set to minimize the Euclidean loss between predicted dielectric images and synthesized dielectric images, as we are interested in minimizing the error at every pixel. In equation form, the cost function is as follows:

$$L(\theta)=1/N\Sigma_{i=1}^{N}\|F(t_i,\theta)-d_i)\|^2, \quad (7)$$

where $d_i$ is the synthesized dielectric image patch, $t_i$ is the MR T1 image patch, N is the batch size, and θ consists of all of the parameters to be learned. The minimization of the cost function is achieved by a gradient-based method with an adaptive moment estimation (adam) using Caffe framework [34]. Momentums are 0.9 and 0.99 and the base learning rate is fixed at 0.0001. The learning process is stopped after 300,000 iterations, which roughly equals 175 epochs.

During testing, the full size MR T1 image (240×240) is passed as an input to the CNN. The input images (240×240) to each convolution layer are zero-padded (to handle boundaries for the convolution process) to ensure that the size of the output images remains the same (240×240). Then the final pooling layer downsamples the predicted image to our desired resolution. For a given MR T1 image, such as the one shown in FIG. 12(A), the network produces a predicted dielectric image as shown in FIG. 12(B), which is visually very similar to the target synthesized $\epsilon$ image, as shown in FIG. 12(C). The differential image between the synthesized E image and the CNN predicted $\epsilon$ image is shown in FIG. 12(F).

Quantitatively, the mean absolute error per pixel for predicted $\epsilon$ image is 0.88. Similarly, predicted σ is generated by the CNN model and the mean absolute error per pixel is 0.026. Given that the brain's relative permittivity value (as high as 70) is larger than that of σ (as high as 3), both predicted images are quantitatively very close to their respective synthesized images. In the first two Conv-Prelu layers, different filters have strong responses for different parts of the brain which mimics the segmentation process. In addition, some parts of the brain show strong responses in several filters, which generates the 'multivalue' (see FIG. 13) non-linear mapping function between MR T1 values and dielectric values. These different responses are combined together in the final Conv-Prelu layer and then downsampled with the pooling layer to produce a predicted $\epsilon$ image at 4 mm as shown in FIG. 12(B).

Figure 13:
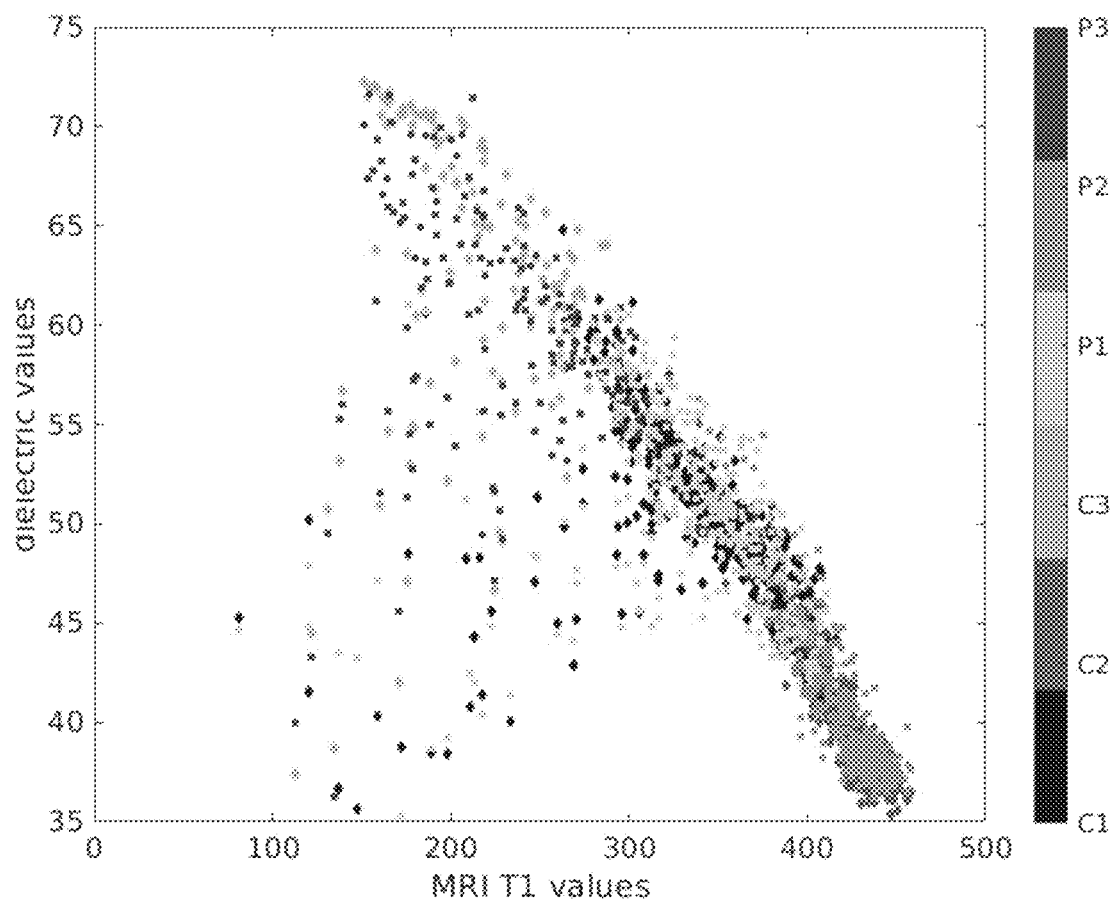
FIG. 13: Evaluation of the learning for one sample image. In color bar, C1 represents grey matter, C2 represents white matter, and C3 represents CSF. All are extracted from synthesized dielectric image at 4 mm resolution. P1 represents predicted grey matter, P2 represents predicted white matter, and P3 represents predicted CSF. All are extracted from the predicted dielectric image at 4 mm resolution.
Figure 14A:
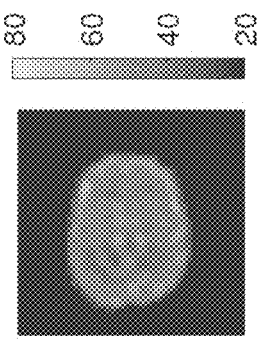
FIGS. 14A, 14B, 14C, 14D, 14E, 14F, 14G, 14H, 14I, and 14J: 4 mm resolution single frequency reconstruction results of patient ABB slice 85. The first row are $\epsilon$ images and the second row are $\sigma$ images. First column are the true dielectric images. Second column are CNN predicted dielectric images. Third column are the recovered images starting from CNN predicted image. Fourth column are the recovered images starting from brain phantom filled with average tissue value.
Figure 14B:
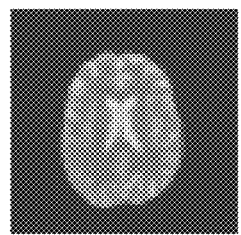
Figure 14C:
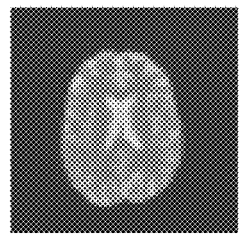
Figure 14D:
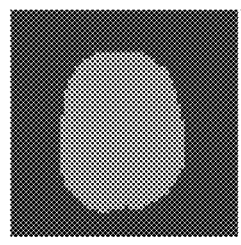
Figure 14E:
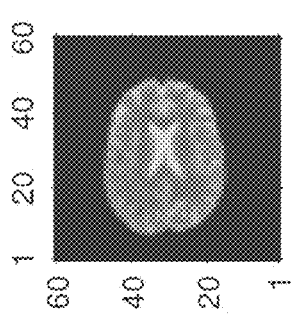
Figure 14F:
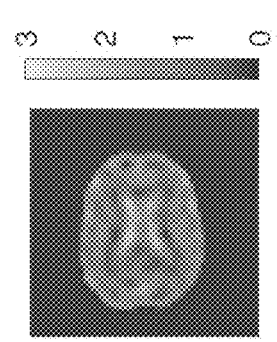
Figure 14G:
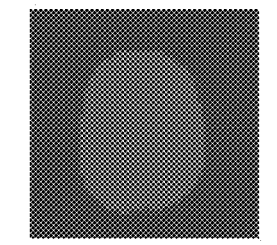
Figure 14H:
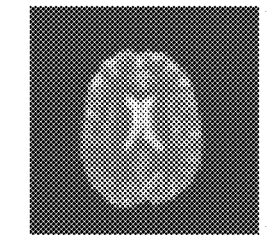
Figure 14I:
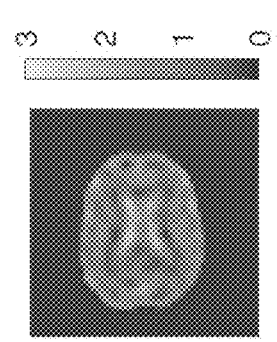
Figure 14J:
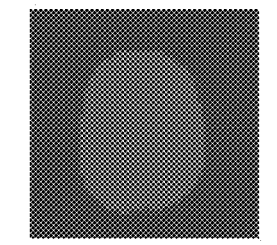

Finally, MR T1 image pixel values are plotted against both synthesized $\epsilon$ and predicted $\epsilon$ image pixel values in FIG. 13. All these images are downsampled to the same 4 mm spatial resolution. In FIG. 13, we compare how well the location of the T1-synthesized E points matches the location of the T1-predicted E points, which could provide us a visual evaluation of the CNN learning this nonlinear mapping function. The figure shows that our learning approach is able to map closely not only the points, which lie within a 'curve', but also those points, that are sparsely scattered.

4. Microwave Imaging with Inverse Scattering

In section 3, the physics-based microwave differential inverse scattering method to further reconstruct the brain dielectric images based on the MR T1 and CNN predicted brain dielectric images is discussed. Reconstruction of the 2D brain dielectric images will be demonstrated. Stacking the predicted 2D dielectric images to create a predicted 3D dielectric brain phantom and performing 3D microwave imaging should follow similar procedures, which are part of our ongoing work and out of the scope of this paper. In differential microwave inverse scattering, the differential scattered fields are produced by the differential dielectrics between the patients' true dielectric brain image and the imaging background. In the proposed method here, the imaging background is the CNN predicted brain dielectric image of the patient. The differential scattered fields are linked to the differential dielectrics through the volume integral equation, which is shown below [26], $$\Delta E_s(r)=k_0^2\int G(r',r)E_t(r')\Delta\chi(r')dV' \quad (8)$$

where r is the observation position vector, r' is the object domain position vector, V' is the domain of the patient's brain, and $k_0$ is the free space wavenumber. The vector $E_t$ is the total electric field inside the true dielectric map of the brain. The quantity G is the numerical vector Green's function, which can link the total field and differential dielectrics to the scattered field measurement in an inhomogeneous background. The $\Delta\chi$ is the differential dielectrics between the true patient brain dielectric map and the predicted dielectric map. It should have the form of (2) and (5) for single frequency and multi-frequency reconstruction, respectively. The vector $\Delta E_s$ is the differential scattered electric field produced by $\Delta\chi$. Starting from the predicted brain dielectrics, the Born iterative method (BIM) is used for the dielectric image reconstruction; as described in W. C. Chew and Y.-M. Wang, "Reconstruction of two-dimensional permittivity distribution using the distorted born iterative method," *IEEE transactions on medical imaging*, vol. 9, no. 2, pp. 218-225, 1990; the entire disclosure of which is hereby incorporated by reference in its entirety.

To solve the inverse scattering problem, the cost function is formulated to calculate the $L_2$ norm of the residuals between the left-hand-side and right-hand-side of (8):

$$F(\Delta\chi)=\|\Delta E_s-\overline{A}\Delta\chi\|^2 \quad (9)$$

where $\overline{A}$ contains the product of $k_0^2$, G and $E_t$. We assume that the location of the brain in the imaging domain is a known prior, and the reconstruction region of $\Delta\chi$ is limited within the brain. A Gaussian white noise is added to the measured scattered electric field $\Delta E_s$. The signal to noise ratio (SNR) used here is the ratio of the scattered field energy to the added noise energy. For all of the cases below, the noise level is set at 90 dB below the transmit power, creating a −90 dB noise floor in the S-parameter measurements, which is conservatively within the limits of typical network-analyzer-based systems [35]. With regard to the measured scattered field, this noise level creates a 20 dB or better SNR, which is consistent with past investigations such as [17]. In every BIM iteration, the $E_t$ is evaluated computationally using a finite-difference time-domain (FDTD) solver and the estimated dielectric properties χ from the previous iteration. Then to solve for $\Delta\chi$, the cost function (9) is minimized with the conjugate gradient (CG) method. We stop the CG iteration if one of the three stopping criteria below is met. (1) the residual of (9) reaches the noise level, (2) the relative change of the residual is less than 0.1%, (3) the CG has reached a maximum of 150 iterations. The CG in almost all of the cases demonstrated below is stopped due to the first two stopping criteria.

To quantitatively analyze the dielectric imaging results, we define the average pixel error for the reconstructed $\epsilon$ and σ images as $$P_{err}^{\epsilon} = \frac{1}{N}\Sigma_{i=1}^{N}|\epsilon^{rec}(i) - \epsilon^{true}(i)| \quad (10)$$

$$P_{err}^{\sigma} = \frac{1}{N}\Sigma_{i=1}^{N}|\sigma^{rec}(i) - \sigma^{true}(i)| \quad (11)$$

where N is the total number of pixels within the reconstructed brain region.

4.1 Generate True Brain Dielectric Image for Simulation

In Section 3, out of the 20 patient cases, we reserved four to test our imaging method. A key challenge in this study is how to acquire the true dielectrics of these four reserved patients' brain images for use in generating the scattered electric fields for our synthetic measurements. In previous MR-assisted multi-modality microwave imaging studies such as [17] [21], the adopted true dielectric phantoms for simulation are synthesized from MR images similarly to our procedures described in Section 2. The main differences between those synthesized dielectric phantoms and the true dielectrics comes from the pixel-level tissue value mapping, which uses a linear mapping function to transfer the inhomogeneity within each tissue type from the MR image to the synthesized dielectric image. However, the per-pixel relationship between MR relaxation time and the dielectrics should be nonlinear. To further model this non-linearity, based on MR synthesized dielectric brain images of the four patients generated with approaches in Section 2, we add a Gaussian distributed random variation to each pixel of the synthesized dielectric image, where 99.6% of these variations should fall within the −10% to +10% range. The [−10%, 10%] random variation range should be sufficient to model the nonlinear mapping effect while keeping the tissue value from deviating far away from its assumed range in [27]. In order to avoid unnatural abrupt jumps between adjacent pixels caused by those variations, we generate those random variation maps using the random rough surface method with Gaussian correlation function described in [36], which models the continuous variation and inhomogeneity of a natural surface. As an example, for patient ABB, we show the 4 mm resolution synthesized dielectric $\epsilon$ images in FIG. 12(C) and the random variation map in FIG. 12(D). By multiplying FIG. 12(C) and FIG. 12(D), the derived true $\epsilon$ image is shown in FIG. 12(E). While our derived true brain dielectric image should be more realistic than the synthesized brain dielectric image, it can also be seen in FIGS. 12(F) and (G) that the difference between the true and predicted $\epsilon$ image is clearly larger than the difference between the synthesized and the predicted $\epsilon$ image, which makes the inversion more challenging and could better test the upper limit of the image reconstruction capability of our proposed method.

4.2 Single-Frequency 4 mm Resolution Reconstruction

In this section, we present the single frequency, 4 mm resolution differential dielectric brain imaging results using BIM with a starting background of a CNN-predicted dielectric image and a brain phantom populated with average brain dielectric values. We place 32 transmitters and 32 receivers working at 1.2 GHz around the dielectric brain phantom, and obtain the scattered electric field measurements with FDTD simulation. To couple the microwave signal into the human head, as might be done in an actual experimental scenario, we choose a coupling fluid with $\epsilon_r=20$ and $\sigma=0.1$. We assume that the exact shape of the human heads used in this study is known a priori and the dielectric image is only reconstructed within the head region. We will demonstrate the reconstruction results of patients ABB and AAB. The image reconstruction of all cases are stopped after 8 BIM iterations. For patient ABB, we demonstrate the inverse scattering image reconstruction results in FIG. 14. As can be seen, the images reconstructed starting from the CNN predicted images are visually very close to the true dielectric images, while the images reconstructed in the conventional way by starting from the phantom with average tissue value are quite unclear and contain little useful information.

To quantitatively analyze the reconstruction result of patient ABB, we plot the scattered field cost function residual error (in dB) and $P_{err}$ in FIG. 15. As can be seen, the inverse scattering physics model can further reduce the $P_{err}$ starting from the CNN predicted image, which shows the merit of the physics model. The $P_{err}$ of $\epsilon$ and $\sigma$ are reduced from 1.86 to 1.50 and 0.079 $P_{err}$ to 0.076, which shows a 20% and 3.8% accuracy improvements respectively. When starting from an average tissue value phantom, the physics model can reduce the of $\epsilon$ and $\sigma$ to 5.5 and 0.29, $P_{err}$ which are significantly higher. One interesting phenomenon is that the scattered field residual error and $P_{err}$ for the average tissue value background case are decreasing with each BIM iteration, while, for the CNN-predicted background case, there is negligible reduction with BIM iterations. As the BIM is designed to overcome the nonlinearity of the microwave inverse scattering problem, this phenomenon demonstrates that the CNN-predicted initial dielectric images are sufficiently close to the true dielectric image that the CNN step has effectively moved the inverse scattering problem from the nonlinear region to the linear region.

Among the four patients reserved for testing, the predicted dielectric image of patient AAB has the largest prediction error. In FIG. 16, we demonstrate the inverse scattering image reconstruction result of patient AAB. As can be seen, the predicted dielectric image is missing the contrast in the bottom part of the figure, which is a large region of tumor, but the physics model is able to recover part of the missing contrast. The reason that the CNN could not accurately predict the tumor region is partially due to the lack of learning examples of tumor in the training data. As can be seen in FIG. 4, the number of voxels belonging to tumor is significantly smaller than that for the three other tissue types. Since glioma tumors can be very dielectrically heterogeneous and we only did a rough estimation of its dielectric value due to lack of measurement data, there is limited useful tumor information for the CNN to learn. In future work, we would update our training data with this inverse scattering model refined dielectric image to let the CNN dynamically evolve and absorb the missing knowledge recovered by the physics model.

The quantitative analysis results of patient AAB are plotted in FIG. 17. As can be seen, for the case of starting from CNN predicted image, the $P_{err}$ of $\epsilon$ and $\sigma$ are reduced from 3.11 to 2.38 and from 0.179 to 0.156, which shows 23.5% and 12.9% accuracy improvements, respectively. For the case of starting from a conventional phantom with an average tissue value, the final $P_{err}$ of $\epsilon$ and $\alpha$ are 6.35 and 0.38, which are much higher than the case with CNN prediction. Lastly, these results also demonstrate that the CNN-predicted dielectric image is again of sufficient quality to significantly reduce the nonlinearity of the inverse scattering problem.

4.3 Single- and Multi-Frequency 2 mm Resolution Reconstruction

In this section, the 2 mm resolution inverse scattering reconstruction using single frequency and multi-frequency measurements is demonstrated. Compared with 4 mm resolution image reconstruction, the 2 mm higher resolution image reconstruction is more difficult with many more unknowns. Thus, using more measurements in the inversion would be desirable to help reduce the ill-posedness of the problem. We propose to use measurements at multiple frequencies to improve the imaging result. Due to the dispersive nature of tissue, when using multiple frequencies for inversion, a basic dielectric model such as that in (2) is insufficient to model the tissue dielectric. Here we use the single-pole Debye model of (5) for the wideband inverse scattering imaging. We use 36 transmitters and 36 receivers surrounding the brain to take the measurements. Four frequency points at 800 MHz, 1.2 GHz, 1.6 GHz and 2 GHz are used for the multi-frequency imaging. To couple the electromagnetic energy into the brain, a coupling fluid in the background is used with dielectric properties of $\epsilon_\infty=2$, $\Delta\epsilon=18$, and $\sigma_d=0.01$. To compare with the multi-frequency reconstruction, we also perform a 2 mm resolution dielectric imaging using only a single frequency signal at 1.2 GHz. Then we compare the reconstructed brain $\epsilon$ and $\sigma$ images at 1.2 GHz using only one frequency versus all four frequencies. The $\epsilon$ and $\sigma$ at 1.2 GHz can be easily computed from the reconstructed Debye model image using the equations below.

$$\epsilon = \text{Re}\{\chi_d(f)\}|_{f=1.2\,GHz},$$

$$\sigma = \text{Im}\{\chi_d(f)\}2\pi f\epsilon_0|_{f=1.2\,GHz} \quad (12)$$

In this section, we demonstrate the single-frequency and multi-frequency 2 mm resolution reconstruction of patient AAB is demonstrated. This experiment among the 4 patients for testing, has the largest $P_{err}$ in the CNN predicted dielectric images, and thus is the most challenging case for the physics-based inverse scattering model. The 2 mm reconstruction with a brain phantom populated with average tissue dielectric as the starting background for iterative reconstruction was also tested. This experiment did not recover any meaningful information just as in the 4 mm resolution case.

Figures 18A, 18B, 18C:
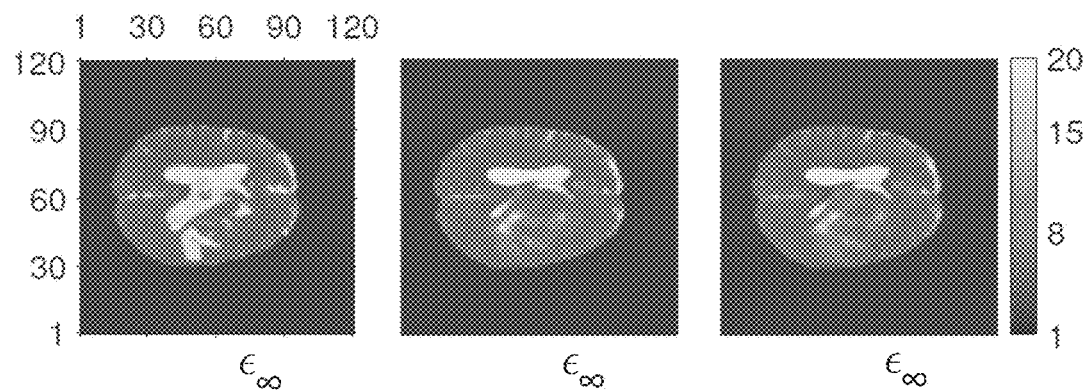
FIGS. 18A, 18B, 18C, 18D, 18E, 18F, 18G, 18H, and 18I: 2 mm resolution 4 frequencies Debye model reconstruction results of patient AAB slice 90. The first, second and third row are the $\epsilon\_\infty$, $\Delta\epsilon$ and $\delta\_d$ images respectively. The first, second and third column are the true, CNN predicted and the reconstructed dielectric images.
Figures 18D, 18E, 18F:
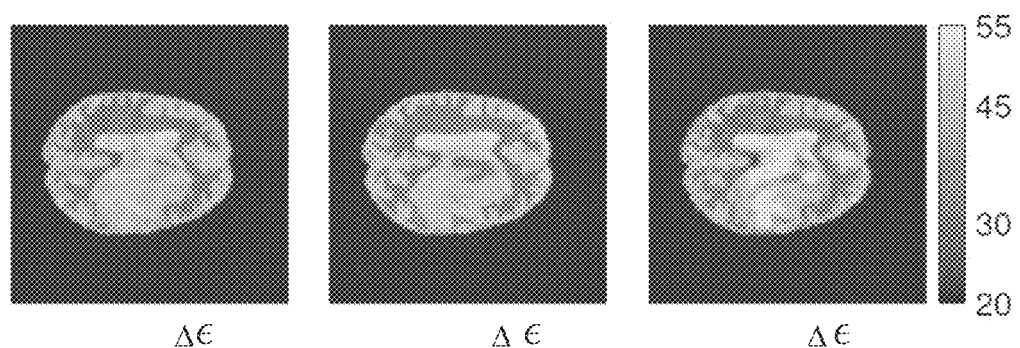
Figures 18G, 18H, 18I:
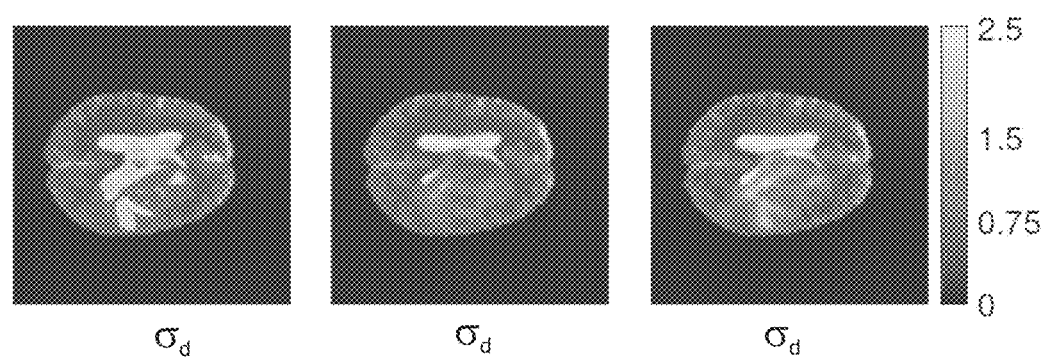
Figures 19A, 19B, 19C, 19D:
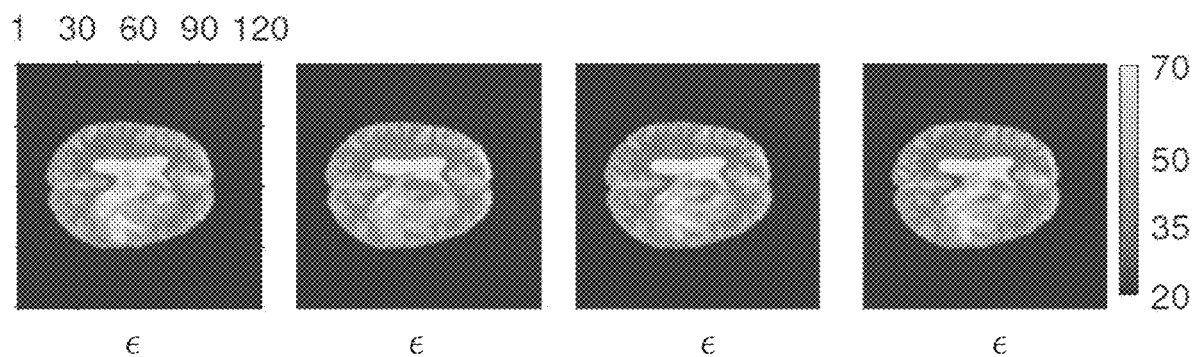
FIGS. 19A, 19B, 19C, 19D, 19E, 19F, 19G, and 19H: 2 mm resolution reconstruction results of patient AAB slice 90. The first and second row are 1.2 GHz $\epsilon$ and $\sigma$ images respectively. The first column are the 1.2 GHz true dielectric images derived from true Deybe model dielectric images of first column of FIG. 17. The second column are the 1.2 GHz CNN predicted dielectric images derived from the CNN predicted Debye model dielectric images from second column of FIG. 17. The third column are the reconstructed 2 mm resolution dielectric images using only 1.2 GHz signal. The forth column are the dielectric images at 1.2 GHz from the reconstructed Debye model dielectric images (the third column of FIG. 17) using 4 frequencies in reconstruction.
Figures 19E, 19F, 19G, 19H:
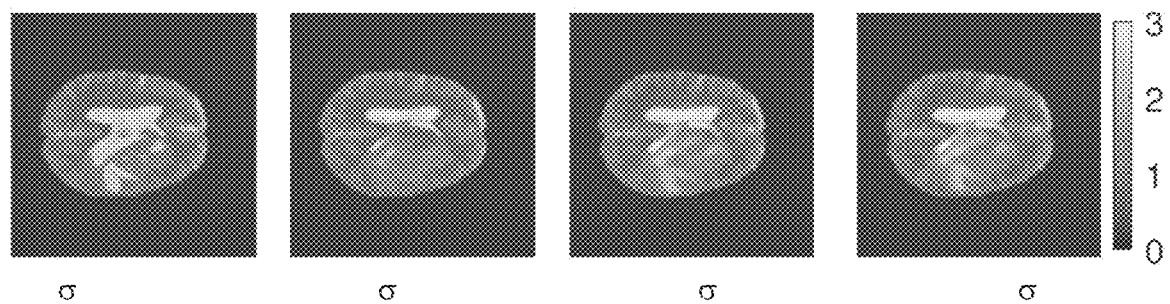

In Section 3, 3 CNNs are trained to predict $\epsilon_\infty$, $\Delta\epsilon$, and $\sigma_d$ images from MR T1 images. To generate the true dielectric images for these 3 Debye parameters for patient AAB, we use the same method described in Section 4.1. The true, CNN-predicted and reconstructed Debye model dielectric images are shown in FIG. 18. To get their corresponding $\epsilon$ and $\sigma$ images at 1.2 GHz, FIGS. 18 (C), (F), and (I) are transformed to the 1.2 GHz $\epsilon$ image (FIG. 19(D)) and a $\sigma$ image (FIG. 19(H)) using (12).

For a fair comparison, the true and predicted dielectric images for the 2 mm resolution 1.2 GHz single frequency reconstruction are generated by transforming the Debye model images to their corresponding 1.2 GHz $\epsilon$ and $\sigma$ images with (12). Then, the 2 mm resolution dielectric images are reconstructed using only the 1.2 GHz signal. As shown in FIG. 19, both the single and multiple frequency reconstructions can partially recover the missing information in the CNN predicted dielectric images, while the multi-frequency reconstruction recovers more contrast and better structure.

The quantitative analysis results are shown in FIG. 20. For the case of single frequency reconstruction, the $P_{err}$ of the 1.2 GHz $\epsilon$ and $\sigma$ are reduced from 3.44 to 2.59 and from 0.20 to 0.17, respectively, which corresponds to a 24.7% and 15% accuracy improvement. For the case of 4-frequency reconstruction, the $P_{err}$ of the 1.2 GHz $\epsilon$ and $\sigma$ are reduced from 3.44 to 2.11 and from 0.20 to 0.15, which corresponds to a 38.7% and 25% accuracy improvement. This comparison has shown the importance of the physics model in the emerging era of data-driven image reconstruction. Even though the CNN has significantly reduced the non-linearity of inversion model and brought the problem to the linear region, a physics model, which can utilize independent measurement information such as from multi-frequency microwave scattering observations is needed to significantly improve the inversion results.

5. Summary

Variation of the present method provide a CNN-assisted multi-modality dielectric imaging method, which uses CNN to effectively incorporate the information from images acquired using other imaging modalities into the model-based microwave inverse scattering imaging process. This method can significantly reduce the nonlinearity and ill-posedness of the microwave imaging problem and can generate dielectric images with significantly improved quality compared with traditional microwave imaging methods. Compared with other multi-modality microwave imaging method, the proposed CNN-assisted method avoids the necessity of performing tissue segmentation for each new patient and could transfer more detailed pixel-level tissue property information from other modalities' images into the microwave imaging process. Although the method for MR-assistance is demonstrated, it can apply to any other modality for which a dielectric mapping can be obtained.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES

[1] R. Chandra, H. Zhou, I. Balasingham, and R. M. Narayanan, "On the Opportunities and Challenges in Microwave Medical Sensing and Imaging," *IEEE Transactions on Biomedical Engineering*, vol. 62, no. 7, pp. 1667-1682, July 2015.

[2] X. Chen, Computational Methods for Electromagnetic Inverse Scattering. Hoboken, N.J., USA: Wiley, March 2018.

[3] M. Moghaddam and W. C. Chew, "Nonlinear two-dimensional velocity profile inversion using time domain data," *IEEE Transactions on Geoscience and Remote Sensing*, vol. 30, no. 1, pp. 147-156, 1992.

[4] W. C. Chew and Y.-M. Wang, "Reconstruction of two-dimensional permittivity distribution using the distorted born iterative method," *IEEE transactions on medical imaging*, vol. 9, no. 2, pp. 218-225, 1990.

[5] P. M. Van Den Berg and R. E. Kleinman, "A contrast source inversion method," *Inverse problems*, vol. 13, no. 6, p. 1607, 1997.

[6] U. S. Kamilov, D. Liu, H. Mansour, and P. T. Boufounos, "A recursive born approach to nonlinear inverse scattering," *IEEE Signal Processing Letters*, vol. 23, no. 8, pp. 1052-1056, 2016.

[7] Z. Wei and X. Chen, "Deep-learning schemes for full-wave nonlinear inverse scattering problems," *IEEE Transactions on Geoscience and Remote Sensing*, 2018.

[8] A. Tarantola, *Inverse Problem Theory and Methods for Model Parameter Estimation*. Philadelphia, Pa., USA: SIAM, 2005.

[9] G. Oliveri, P. Rocca, and A. Massa, "A bayesian-compressive-sampling-based inversion for imaging sparse scatterers," *Geoscience and Remote Sensing, IEEE Transactions on*, vol. 49, no. 10, pp. 3993-4006, 2011.
[10] P. Shah, U. K. Khankhoje, and M. Moghaddam, "Inverse scattering using a joint l1-l2 norm-based regularization," *IEEE Transactions on Antennas and Propagation*, vol. 64, no. 4, pp. 1373-1384, 2016.
[11] G. Chen, P. Shah, and M. Moghaddam, "Multi-parameter microwave inverse scattering with group sparsity constraints," in Proc. IEEE Int. Symp. Antennas Propag. USNC/URSI Nat. Radio Sci. Meeting, July 2018, pp. 697-698.
[12] O. Dorn, E. L. Miller, and C. M. Rappaport, "A shape reconstruction method for electromagnetic tomography using adjoint fields and level sets," *Inverse problems*, vol. 16, no. 5, p. 1119, 2000.
[13] P. Shah and M. Moghaddam, "A fast level set method for multimaterial recovery in microwave imaging," *IEEE Transactions on Antennas and Propagation*, vol. 66, no. 6, pp. 3017-3026, 2018.
[14] S. Caorsi and P. Gamba, "Electromagnetic detection of dielectric cylinders by a neural network approach," *IEEE transactions on geoscience and remote sensing*, vol. 37, no. 2, pp. 820-827, 1999.
[15] R. Horisaki, R. Takagi, and J. Tanida, "Learning-based imaging through scattering media," *Optics express*, vol. 24, no. 13, pp. 13 738-13 743, 2016.
[16] I. T. Rekanos, "Neural-network-based inverse-scattering technique for online microwave medical imaging," *IEEE transactions on magnetics*, vol. 38, no. 2, pp. 1061-1064, 2002.
[17] D. Kurrant, A. Baran, J. LoVetri, and E. Fear, "Integrating prior information into microwave tomography part 1: Impact of detail on image quality," *Medical physics*, vol. 44, no. 12, pp. 6461-6481, 2017.
[18] M. Omer, P. Mojabi, D. Kurrant, J. LoVetri, and E. Fear, "Proof-of-concept of the incorporation of ultrasound-derived structural information into microwave radar imaging," *IEEE Journal on Multiscale and Multiphysics Computational Techniques*, vol. 3, pp. 129-139, 2018.
[19] P. M. Meaney, A. H. Golnabi, N. R. Epstein, S. D. Geimer, M. W. Fanning, J. B. Weaver, and K. D. Paulsen, "Integration of microwave tomography with magnetic resonance for improved breast imaging," *Medical physics*, vol. 40, no. 10, 2013.
[20] A. H. Golnabi, P. M. Meaney, S. D. Geimer, and K. D. Paulsen, "Comparison of no-prior and soft-prior regularization in biomedical microwave imaging," *Journal of Medical Physics/Association of Medical Physicists of India*, vol. 36, no. 3, p. 159, 2011.
[21] L. M. Neira, B. D. Van Veen, and S. C. Hagness, "High-resolution microwave breast imaging using a 3-d inverse scattering algorithm with a variable-strength spatial prior constraint," *IEEE Transactions on Antennas and Propagation*, vol. 65, no. 11, pp. 6002-6014, 2017.
[22] A. H. Golnabi, P. M. Meaney, and K. D. Paulsen, "3d microwave tomography of the breast using prior anatomical information," *Medical physics*, vol. 43, no. 4, pp. 1933-1944, 2016.
[23] R. Li, W. Zhang, H.-I. Suk, L. Wang, J. Li, D. Shen, and S. Ji, "Deep learning based imaging data completion for improved brain disease diagnosis Med Image Comput Comput Assist Interv., vol. 17, no. Pt 3, pp. 305-312, 2014.
[24] X. Han, "MR-based synthetic CT generation using a deep convolutional neural network method," Med. Phys., vol. 44, no. 4, pp. 1408-1419, 2017.
[25] D. Nie, R. Trullo, J. Lian, L. Wang, C. Petitjean, S. Ruan, Q. Wang, and D. Shen, "Medical Image Synthesis with Deep Convolutional Adversarial Networks," *IEEE Transactions on Biomedical Engineering*, vol. 65, no. 12, pp. 2720-2730, December 2018.
[26] W. C. Chew, *Waves and Fields in Inhomogenous Media*. Piscataway, N.J., USA: IEEE Press, 1995.
[27] S. Gabriel, R. W. Lau, and C. Gabriel, "The dielectric properties of biological tissues: III. Parametric models for the dielectric spectrum of tissues," Phys. Med. Biol., vol. 41, no. 11, p. 2271, 1996.
[28] B. H. Menze, A. Jakab, S. Bauer, J. Kalpathy-Cramer, K. Farahani, J. Kirby, Y. Burren, N. Porz, J. Slotboom, R. Wiest et al., "The multimodal brain tumor image segmentation benchmark (brats)," *IEEE transactions on medical imaging*, vol. 34, no. 10, p. 1993, 2015.
[29] J. Ashburner and K. J. Friston, "Unified segmentation," *Neuroimage*, vol. 26, no. 3, pp. 839-851, 2005.
[30] W. D. Penny, K. J. Friston, J. T. Ashburner, S. J. Kiebel, and T. E. Nichols, Statistical Parametric Mapping: The Analysis of Functional Brain Images. Amsterdam, The Netherlands: Elsevier, 2011.
[31] E. Zastrow, S. K. Davis, M. Lazebnik, F. Kelcz, B. D. Van Veen, and S. C. Hagness, "Development of anatomically realistic numerical breast phantoms with accurate dielectric properties for modeling microwave interactions with the human breast," IEEE Trans. Biomed. Eng., vol. 55, no. 12, pp. 2792-2800, December 2008.
[32] Y. Lu, B. Li, J. Xu, and J. Yu, "Dielectric properties of human glioma and surrounding tissue," Int. J. Hyperthermia, vol. 8, no. 6, pp. 755-760, December 1992.
[33] C. Dong, C. C. Loy, K. He, and X. Tang, "Learning a deep convolutional network for image super-resolution," in Proc. Eur. Conf. Comput. Vis. Cham, Switzerland: Springer, 2014, pp. 184-199.
[34] Y. Jia, E. Shelhamer, J. Donahue, S. Karayev, J. Long, R. Girshick, S. Guadarrama, and T. Darrell, "Caffe: Convolutional architecture for fast feature embedding," arXiv preprint arXiv: 1408.5093, 2014.
[35] M. Haynes, J. Stang, and M. Moghaddam, "Real-time microwave imaging of differential temperature for thermal therapy monitoring," IEEE Trans. Biomed. Eng, vol. 61, no. 6, pp. 1787-1797, June 2014.
[36] X. Duan and M. Moghaddam, "Bistatic Vector 3-D Scattering From Layered Rough Surfaces Using Stabilized Extended Boundary Condition Method," *IEEE Transactions on Geoscience and Remote Sensing*, vol. 51, no. 5, pp. 2722-2733, May 2013.

What is claimed is:
1. A method for constructing dialect images in a digital medium environment, the method comprising:
training a convolutional neural network to learn a complex mapping function from patient non-dielectric images to dielectric images at a single frequency or multiple frequencies, the convolutional neural network being trained with a test set derived from characterized images;
applying the trained convolutional neural network to a subject's non-dielectric imaging data to determine an initial predicted dielectric image; and
applying the initial predicted dielectric image as a starting input for a physics-model-based iterative dielectric image reconstruction model to form a final predicted dielectric image where non-dielectric imaging data and initial predicted dielectric image can be at the same spatial resolution or at a different spatial resolution.

2. The method of claim 1 wherein the patient non-dielectric images are selected from the group consisting of magnetic resonance images, computed tomography images, ultrasound images, and combination thereof.

3. The method of claim 1 wherein the physics-model-based iterative dielectric image reconstruction model is a microwave differential inverse scattering model.

4. The method of claim 1 wherein the test set includes pairs of non-dielectric images and corresponding synthetic dielectric images.

5. The method of claim 4 wherein the corresponding synthetic dielectric images are a set of dielectric images derived from data obtained in a prior imaging study independent of an imaging study used to form a set of non-dielectric images.

6. The method of claim 4 wherein the corresponding synthesized dielectric images are formed by segmenting imaging data from a prior clinical imaging study into different tissue types and then mapping previously determined corresponding dielectric values for each tissue type.

7. The method of claim 6 wherein magnetic resonance T1 images are acquired via actual MR scans and a set of corresponding dielectric images is synthesized from the magnetic resonance T1 images or from co-registered images from a different imaging technique.

8. The method of claim 7 wherein the different imaging technique is selected from the group consisting of magnetic resonance T2 scans, computerized tomography, ultrasound, and other imaging sequences.

9. The method of claim 4 wherein T2 images are applied for segmentation to get different tissue type regions and map each tissue type being mapped to its measured dielectric values to create the corresponding synthesized dielectric images.

10. The method of claim 4 wherein non-dielectric images are magnetic resonance images, computed tomography images, ultrasound images, and/or combinations thereof.

11. The method of claim 4 wherein non-dielectric images are T1 magnetic resonance images or T2 magnetic resonance images.

12. The method of claim 4 wherein the non-dielectric images and their corresponding reconstructed dielectric images are used as an additional set of image pairs to train the convolutional neural network.

13. The method of claim 1 wherein the test set includes pairs of non-dielectric image data and corresponding experimental dielectric image data.

14. The method of claim 13 wherein experimental dielectric image data are formed by building layered dielectric tissue phantoms with known dielectric values and which have similar dielectric values to tissues and then acquiring magnetic resonance images of those dielectric phantoms to create magnetic resonance-dielectric image pairs.

15. The method of claim 13 wherein the convolutional neural network is trained in a learning process that is performed iteratively.

16. A system for constructing dialect images, the system comprising:
a computing device configured to receive a subject's non-dielectric imaging data, the computing device including a computer processor configured execute a trained convolutional neural network by training an untrained convolutional neural network to learn a complex mapping function from patient non-dielectric images to dielectric images at a single frequency or multiple frequencies to form the trained convolutional neural network, the untrained convolutional neural network being trained with a test set derived from characterized images, the computer processor also configured to:
apply the trained convolutional neural network to the subject's non-dielectric imaging data to determine an initial predicted dielectric image; and
apply the initial predicted dielectric image as a starting input for a physics-model-based iterative dielectric image reconstruction model to form a final predicted dielectric image where non-dielectric imaging data and initial predicted dielectric image can be at the same spatial resolution or at a different spatial resolution.

17. The system for constructing dialect images of claim 16 wherein the patient non-dielectric images are selected from the group consisting of magnetic resonance images, computed tomography images, ultrasound images, and combination thereof.

18. The system for constructing dialect images of claim 16 wherein the physics-model-based iterative dielectric image reconstruction model is a microwave differential inverse scattering model.

19. The system for constructing dialect images of claim 16 wherein the test set includes pairs of non-dielectric images and corresponding synthetic dielectric images.

20. The system for constructing dialect images of claim 19 wherein the corresponding synthetic dielectric images are a set of dielectric images derived from data obtained in a prior imaging study independent of an imaging study used to form a set of non-dielectric images.

21. The system of claim 19 wherein the corresponding synthesized dielectric images are formed by segmenting imaging data from a prior clinical imaging study into different tissue types and then mapping previously determined corresponding dielectric values for each tissue type.

* * * * *